United States Patent [19]

Ripka

[11] 4,150,135

[45] Apr. 17, 1979

[54] SUBSTITUTED 4A-PHENYL-N-PHENYLALKYL-CIS-DECAHYDROISOQUINOLINES

[75] Inventor: William C. Ripka, Wilmington, Del.

[73] Assignee: E. I. Du Pont de Nemours and Company, Wilmington, Del.

[21] Appl. No.: 774,436

[22] Filed: Mar. 4, 1977

Related U.S. Application Data

[63] Continuation-in-part of Ser. No. 599,461, Aug. 1, 1975, which is a continuation-in-part of Ser. No. 504,302, Sep. 9, 1974, abandoned.

[51] Int. Cl.$^2$ .................... A61K 31/47; C07D 217/04
[52] U.S. Cl. .................................. 424/258; 546/144; 546/142; 260/465 D; 260/591; 560/102
[58] Field of Search ............ 260/287 D, 288 CE, 288, 260/283, 289; 424/258

[56] References Cited

U.S. PATENT DOCUMENTS

| | | | |
|---|---|---|---|
| 2,740,788 | 4/1956 | Grüssner et al. | 260/289 R |
| 3,546,227 | 12/1970 | Gmünder et al. | 260/289 R |
| 3,666,763 | 5/1973 | Grethe et al. | 260/289 R |

FOREIGN PATENT DOCUMENTS

| | | |
|---|---|---|
| 802557 | 7/1973 | Belgium .............................. 260/289 D |
| 4431582 | 12/1969 | Japan. |
| 1164192 | 8/1966 | United Kingdom. |

OTHER PUBLICATIONS

Boekelheide et al., JACS 72, 712 (1950).
Eddy, "J. of the Am. Pharm. Assoc.", May 1950, pp. 245ff.
Finch et al., "J. Org. Chem" 39, No. 8, 1118–1124, Apr. 19, 1974.
Boekelheide et al., JACS 72, 712 (1950).
Finch et al., "J. Org. Chem" 39, No. 8, 1118–1124, Apr. 19, 1974.

*Primary Examiner*—Donald G. Daus
*Assistant Examiner*—David E. Wheeler

[57] ABSTRACT

4a-Aryl-cis-decahydroisoquinolines, such as N-phenethyl-4a-(m-hydroxyphenyl)-cis-decahydroisoquinoline, useful as analgesics.

31 Claims, No Drawings

SUBSTITUTED 4A-PHENYL-N-PHENYLALKYL-CIS-DECAHYDROISOQUINOLINES

CROSS-REFERENCE TO RELATED APPLICATIONS

This application is a continuation-in-part of my application Ser. No. 599,461 filed Aug. 1, 1975 which is a continuation-in-part of my application Ser. No. 504,302 filed Sept. 9, 1974, now abandoned.

BACKGROUND

This invention concerns the discovery that a selected group of 4a-aryl-cis-decahydroisoquinolines are useful as analgesics, many with little or no addictive properties.

Boekelheide and Schilling, J. Am. Chem. Soc. 72, 712 (1950), disclosed the compound N-methyl-4a-phenyl-cis decahydroisoquinoline, (naming it "N-methyl-10-phenyldecahydroisoquinoline") and indicated that it had low analgesic activity.

The present invention results from efforts to develop new compounds with high analgesic potency and low abuse liability.

SUMMARY

According to this invention there is provided novel compounds of formula I and their suitable pharmaceutical salts, processes for their manufacture, pharmaceutical compositions containing them, and methods of using them to produce analgesia in mammals.

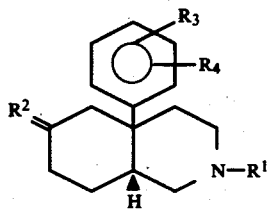

formula I where
  $R_1$ is hydrogen; $C_1$-$C_6$ alkyl; —CH$_2$Y where Y is $C_2$-$C_6$ alkenyl or $C_2$-$C_6$ alkynyl;
  —(CH$_2$)$_m$

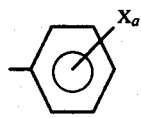

where m is 1 to 4, X is Cl, Br, F, CF$_3$, OCH$_3$, CH$_3$, isopropyl, —NH$_2$, or —N(CH$_3$)$_2$, a=0, 1 or 2;
  —(CH$_2$)$_m$

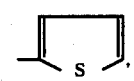

—(CH$_2$)$_m$

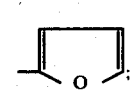

or cycloalkylmethyl of the formula —CH$_2$-CH<((CH$_2$)$_n$, where n is 2–5;
  $R_2$ is divalent oxygen (=O),

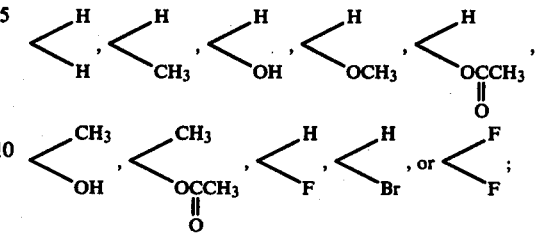

$R_3$ is —OH, —OCH$_3$,

or F;
$R_4$ is —H, —OH, —OCH$_3$,

with the proviso that when $R_3$ is —F, $R_4$ must be —H.

DETAILED DESCRIPTION

Representative $R_1$ groups are methyl, ethyl, propyl, butyl, hexyl, allyl (—CH$_2$CH=CH$_2$), 2-butenyl, 3-butenyl, 4-heptenyl, 3,3-dimethylallyl [—CH$_2$CH=C(CH$_3$)$_2$], propargyl (—CH$_2$C≡CH), phenyl propargyl, heptynyl, benzyl, phenethyl, 4-phenyl-n-butyl[—CH$_2$(C$_2$)$_3$C$_6$H$_5$], cyclopropylmethyl [—CH$_2$CH<(CH$_2$)$_2$], cyclobutylmethyl [—CH$_2$-CH<(CH$_2$)$_3$], cyclohexylmethyl [—CH$_2$CH<(CH$_2$)$_5$], furylmethyl

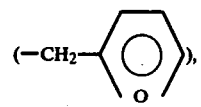

2-furylethyl

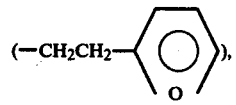

2-thienylethyl

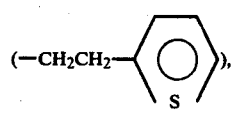

p-methylphenethyl

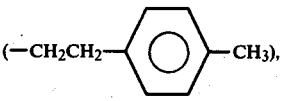

p-fluorophenethyl,

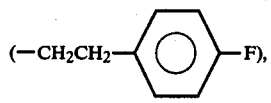

p-methoxyphenethyl

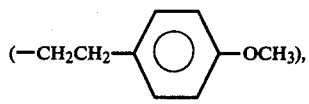

p-chlorophenethyl

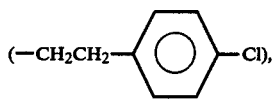

p-aminophenethyl

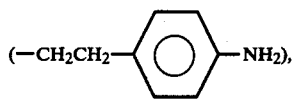

p-dimethylaminophenethyl, and cinnamyl (—CH$_2$CH=CHC$_6$H$_5$).

Representative Ar groups are 3-hydroxyphenyl, 3-methoxyphenyl, 4-methoxyphenyl, 3-acetoxyphenyl, 2,3-dihydroxyphenyl, 3,4-dimethoxyphenyl, 3,4-diacetoxyphenyl, 3-hydroxy-4-methoxyphenyl, 2-methoxy-3-acetoxyphenyl, 3-fluorophenyl and 4-fluorophenyl.

The 4a-aryl-cis-decahydroisoquinolines of formula I include various stereochemical isomers stemming from substitution at position 6, and from optical asymmetry of the whole structure. When monovalent R$^2$ substituents at position 6 are different (e.g., when

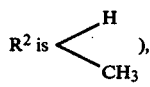

spatial considerations require the existence of axial and equatorial isomers. In the molecule as a whole, spatial considerations require the existence of d and l optical isomers. These are normally present as racemic mixtures which can be resolved by known methods (Eliel, Stereochemistry of Carbon Compounds, McGraw-Hill, 1962, p. 31).

Pharmaceutically suitable acid addition salts of these compounds include those made with physiologically acceptable acids that are known in the art; such salts include hydrochloride, sulfate, phosphate, nitrate, citrate, maleate and the like.

PREFERRED COMPOUNDS

The analgesic compounds preferred because of their high level of activity are those where
R$^1$ is

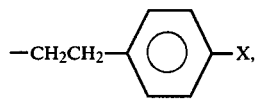

X=H or CH$_3$ with CH$_3$ being more preferred;
R$^2$ is

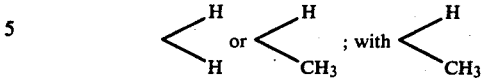

being more preferred;
R$^3$ is m-OH or m-OCH$_3$; and
R$^4$ is H.

Most preferred because of their activity are N-(p-tolylethyl)-4a-m-hydroxyphenyl-6β-cis-decahydroisoquinoline and N-(phenethyl)-4a-m-methoxyphenyl-cis-decahydroisoquinoline.

Synthesis

The multi-step processes of the invention start with 2-cyano-3-aryl-3-carbalkoxymethylcyclohexenes which can be obtained according to procedures disclosed by Boekelheide and Schilling (loc. cit.) with respect to 2-cyano-3-phenyl-3-carbethoxymethylcyclohexene (cf, Example 1, Part A). Reaction of a 2-cyano-3-aryl-3-carbalkoxymethylcyclohexene with hydrogen chloride in a lower alkanol such as ethanol forms a 4a-aryl-1,3-diketo-1,2,3,4,4a,5,6,7-octahydroisoquinoline (cf, Example 1, Part B). These 1,3-diketo-octahydroisoquinolines possess a conformational arrangement of the fused rings which requires formation of trans-decahydroisoquinoline structures when the 8,8a- double bond is converted to a single bond (cf, Example 1, Part D; Example 6, Part A). A key step in the invention is the novel isomerization of a 1,3-diketo-trans-decahydroisoquinoline to the cis isomer in the presence of a relatively strong base (cf, Example 1, Part E; Example 4, Part A).

The selection of specific preparational steps following the initial formation of a 1,3-diketo-1,2,3,4,4a,-5,6,7-octahydroisoquinoline depends upon the specific 4a-aryl-cis-decahydroisoquinoline derivative that is desired. The sequence involves at least three steps, A, B, and C, which are illustrated below. Compounds having no unsaturated carbon to carbon bonds in R$^1$ (R$^{1a}$ in process steps) are prepared by steps A, B-1, and C. Compounds having saturated or unsaturated carbon to carbon bonds in R$^1$ are prepared by steps A, B-2, and C.

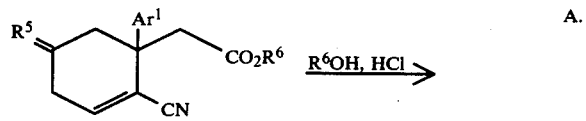

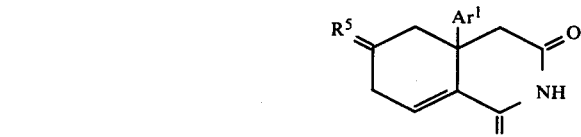

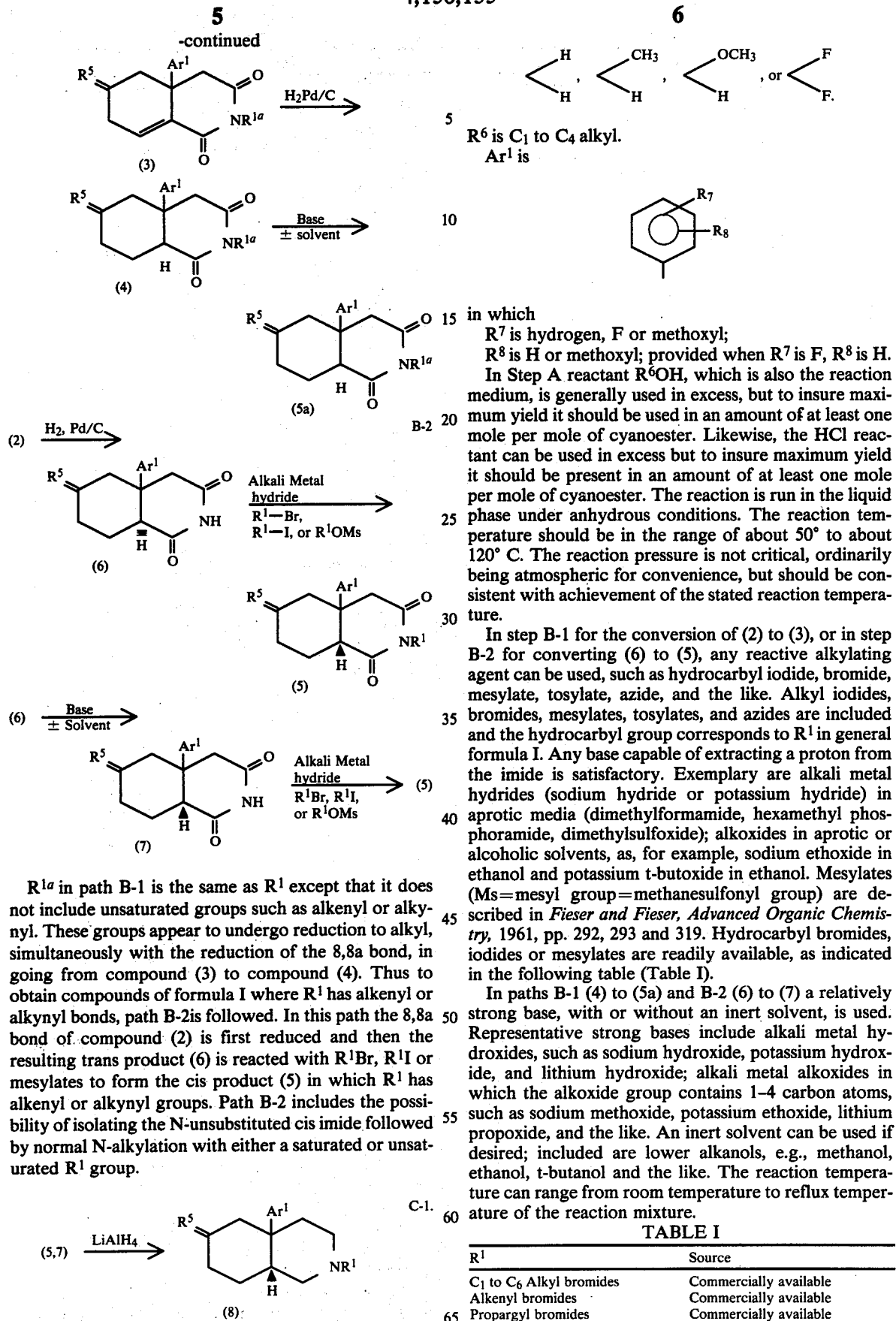

In the foregoing formulas (1) through (8), the groups $R^1$ have the values given previously. $R^5$ is $$\underset{H}{\overset{H}{<}}, \underset{H}{\overset{CH_3}{<}}, \underset{H}{\overset{OCH_3}{<}}, \text{ or } \underset{F}{\overset{F}{<}}.$$

$R^6$ is $C_1$ to $C_4$ alkyl.
$Ar^1$ is in which
$R^7$ is hydrogen, F or methoxyl;
$R^8$ is H or methoxyl; provided when $R^7$ is F, $R^8$ is H.

In Step A reactant $R^6OH$, which is also the reaction medium, is generally used in excess, but to insure maximum yield it should be used in an amount of at least one mole per mole of cyanoester. Likewise, the HCl reactant can be used in excess but to insure maximum yield it should be present in an amount of at least one mole per mole of cyanoester. The reaction is run in the liquid phase under anhydrous conditions. The reaction temperature should be in the range of about 50° to about 120° C. The reaction pressure is not critical, ordinarily being atmospheric for convenience, but should be consistent with achievement of the stated reaction temperature.

In step B-1 for the conversion of (2) to (3), or in step B-2 for converting (6) to (5), any reactive alkylating agent can be used, such as hydrocarbyl iodide, bromide, mesylate, tosylate, azide, and the like. Alkyl iodides, bromides, mesylates, tosylates, and azides are included and the hydrocarbyl group corresponds to $R^1$ in general formula I. Any base capable of extracting a proton from the imide is satisfactory. Exemplary are alkali metal hydrides (sodium hydride or potassium hydride) in aprotic media (dimethylformamide, hexamethyl phosphoramide, dimethylsulfoxide); alkoxides in aprotic or alcoholic solvents, as, for example, sodium ethoxide in ethanol and potassium t-butoxide in ethanol. Mesylates (Ms=mesyl group=methanesulfonyl group) are described in *Fieser and Fieser, Advanced Organic Chemistry*, 1961, pp. 292, 293 and 319. Hydrocarbyl bromides, iodides or mesylates are readily available, as indicated in the following table (Table I).

In paths B-1 (4) to (5a) and B-2 (6) to (7) a relatively strong base, with or without an inert solvent, is used. Representative strong bases include alkali metal hydroxides, such as sodium hydroxide, potassium hydroxide, and lithium hydroxide; alkali metal alkoxides in which the alkoxide group contains 1-4 carbon atoms, such as sodium methoxide, potassium ethoxide, lithium propoxide, and the like. An inert solvent can be used if desired; included are lower alkanols, e.g., methanol, ethanol, t-butanol and the like. The reaction temperature can range from room temperature to reflux temperature of the reaction mixture.

TABLE I

| $R^1$ | Source |
|---|---|
| $C_1$ to $C_6$ Alkyl bromides | Commercially available |
| Alkenyl bromides | Commercially available |
| Propargyl bromides | Commercially available |
| 3,3-Dimethylallyl bromides | Commercially available |
| Cyclohexylmethyl bromides | Commercially available |
| Benzyl bromides | Commercially available |
| Phenethyl bromides | Commercially available |

TABLE I-continued

| R¹ | Source |
|---|---|
| 4-Phenyl-n-butyl bromides | Bugrova et al., Zh. obshch. Khim, 32, 3573 (1962) |
| Cyclopropylmethyl bromides | Kirmse et al., Ber., 99, 2855 (1966) |
| Cyclobutylmethyl bromides | Krug et al., J. Am. Chem. Soc., 76, 3222 (1954) |
| Cyclopentylmethyl bromides | Smith et al., J. Org. Chem., 21, 1448 (1956) |
| 2-Furylmethyl bromides | Sharifkanov et al., Khim. Khim Technol (alma-ata) 1971, 80 |
| 2-Furylethyl mesylates | Crossland and Servis, J. Org. Chem. 35, 3195 (1970) |
| 2-Pyridylethyl mesylates | give Procedure for mesylates from alcohols |
| 2-Thienylethyl mesylates | " |
| Substituted phenethyl mesylates | " |

In the preparation of a 2-cyano-3-phenyl-3-carbalkoxymethylcyclohexene, the Boekelheide and Schilling procedure involves preliminary steps starting with cyclohexanone, as follows;

a. Cyclohexanone→2-chlorocyclohexanone (Horning, *Organic Syntheses*, Coll. Vol. III, 1955, p. 188).
b. 2-Chlorocyclohexanone→2-phenylcyclohexanone [Newman et al. J., Am. Chem. Soc. 66, 1551 (1944)].
c. 2-Phenylcyclohexanone→2-phenyl-2-carbethoxycyclohexanone [Newman et al., J. Am. Chem. Soc. 69, 942 (1947)].
d. 2-Phenyl-2-carbethoxycyclohexanone→2-cyano-3-phenyl-3-carbethoxycyclohexene.

Final products corresponding to formula I contain certain groups $R^2$ which do not appear to be compatible with the chemistry of the process steps. The $R^5$ groups, which are stable to the various process steps, are used in the process and at the end of the syntheses are converted to $R^2$ groups.

The preliminary steps above aid in producing various equivalents defined by the various values of Ar and $R^2$ in general formula I through starting with appropriately substituted cyclohexanones in step (a) and with appropriately substituted arylmagnesium bromides as intermediates in step (b). Thus, 4-methylcyclohexanone and 4-methoxycyclohexane, which are commercially available, can be used as basic starting materials to produce compounds of formula I in which

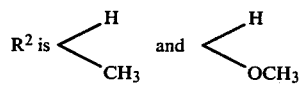

respectively.

The compounds of formula I in which $R_2$ ($R^5$ in the process description) is

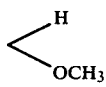

serve as intermediates to compounds of formula I in which $R^2$ had other values. The following table (Table II) shows the additional $R^2$ values and the known methods for obtaining them.

TABLE II

| $R^2$ | Procedure |
|---|---|
| <H, OH | Demethylation of the methoxy compound |
| <H, OCCH₃‖O | Acetylation of the hydroxy compound |
| =O | Oxidation of the hydroxy compound |
| <CH₃, OH | Reaction of the oxo compound with methyllithium |
| <CH₃, OCCH₃‖O | Acetylation of the <CH₃, OH compound |
| <H, Cl | Reaction of the hydroxy compound with a strong chloridation agent, e.g., thionyl chloride. |
| <F, F | Reaction of the oxo compound with sulfur tetraflouride [(Martin et al. J. Org. Chem. 27, 3164 (1962))] |

Likewise, the use of appropriately substituted phenyl bromides in the preparation of the arylmagnesium bromide Grignard reactant for step (b) leads to corresponding Ar groups (Ar¹ in the process description) in the products of formula I. The following table (Table III) shows pertinent Ar¹ groups with substituent $R^7$ and $R^8$ groups as defined above.

TABLE III

| Ar¹ | Source |
|---|---|
| 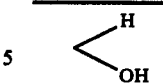 | Bromides in which $R^7$ is hydrogen, fluorine or methoxyl and $R^8$ is hydrogen are commercially available. The bromide in which $R^7$ is hydrogen and $R^8$ is methoxyl is also commercially available. The bromide in which both $R^7$ and $R^8$ are methoxyl is obtainable by the method of Mason, J. Am. Chem. Soc. 69, 2241 (1947). |
| 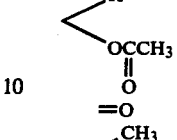 | The bromides in which $R^8$ and $R^7$ are both methoxyl, and in which $R^8$ is hydrogen and $R^7$ is methoxyl or fluorine, are commercially available. The bromide in which $R^8$ and $R^7$ are combined to form dioxymethylene is also commercially available. |

Compounds in which Ar¹ has methoxyl substituents (as in Table III) serve as intermediates to compounds of formula I in which Ar has hydroxyl or acetoxyl substituents by using methods for conversion of $R^5$ groups to $R^2$ groups as shown in Table II. This appears necessary since certain substituents such as OH have to be introduced at the end of the synthesis. Thus Ar¹ contains a methoxyl, or "masked hydroxyl", which is subsequently converted to OH.

Process steps A, B-1 and C are illustrated by Examples 1-3 and process steps A, B-2 and C are illustrated by Examples 4-7, etc.

In the following illustrative examples all parts are by weight and temperatures are in degrees centigrade unless otherwise stated. The nmr spectra were at 60 $H_z$ and resonance positions are described as cps or in ppm from tetramethylsilane (tms).

EXAMPLE 1

N-Methyl-4a-phenyl-cis-decahydroisoquinoline

A. 2-Cyano-3-phenyl-3-carbethoxymethylcyclohexene

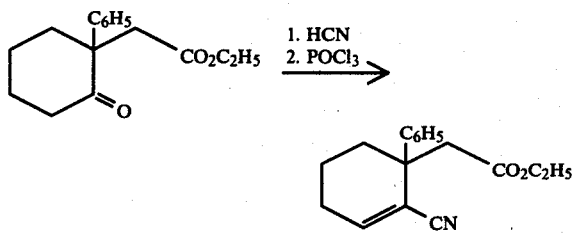

2-Carbethoxymethyl-2-phenylcyclohexanone (Boekelheide, et al., above) (90 g., 0.346 mole), 200 ml of hydrogen cyanide and 12 drops of a saturated aqueous solution of potassium cyanide was stirred at 0° C. overnight. Concentrated sulfuric acid (15 drops) was then added and the excess hydrogen cyanide evaporated. The crude cyanohydrin was taken up in ether and washed with cold 10% sulfuric acid solution, then dried with $Na_2SO_4$ and evaporated. The residual oil was dissolved in 500 ml of pyridine and 100 ml of phosphorus oxychloride was added. The reaction mixture was stirred under nitrogen at reflux for 5 hours then allowed to stand at 25° C. overnight. It was then carefully poured into a mixture of 2 liters of ice-water and 400 ml of concentrated hydrochloric acid and extracted with ether. The ether extract was washed with dilute hydrochloric acid, water and brine, then dried ($Na_2SO_4$) and evaporated. The residual oil was distilled, yielding 45 g of pale yellow liquid, bp 135° C. (0.20 mm), identified as 2-cyano-3-phenyl-3-carbethoxymethylcyclohexene.

NMR ($CDCl_3$): triplet at 64, 71, 78 cps, 3H (—OCH$_2$CH$_3$); methylene envelope from 70–150 cps, ca 6H; singlet at 178 cps, 2H

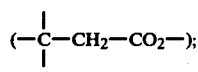

quartet at 234, 242, 249, 256, 2H (—OCH$_2$CH$_3$); triplet at 406, 410, 414, 1H

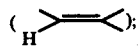

singlet at 436 cps, 5H (aromatic H).
IR (neat): 4.50μ (C≡N); 5.5 and 5.85μ (lactone impurity); 5.75μ (—CO$_2$—).

B. 4a-Phenyl-1,3-diketo-1,2,3,4,4a,5,6,7-Octahydroisoquinoline

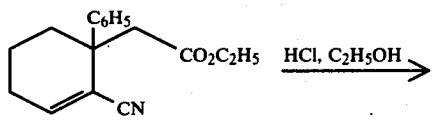

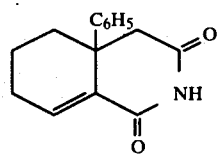

The product of Part A (50 g), dissolved in a minimum amount of absolute ethanol, was added to 2.5 liters of absolute ethanol previously saturated with anhydrous hydrogen chloride. The solution was refluxed under nitrogen for 48 hours. It was then cooled and concentrated to about 300 ml on a rotary evaporator. On cooling, a white crystalline solid precipitated which was filtered, washed with cold ethanol, and dried to yield 25 g (56%) of 4a-phenyl-1,3-diketo-1,2,3,4,4a,5,6,7-octahydroisoquinoline, mp 241°–3°.

Anal. Calcd. for $C_{15}H_{15}NO_2$: C, 74.65; H, 6.26; N, 5.81; Found: C, 74.67; H, 6.25; N, 5.65.

C. N-Methyl-4a-phenyl-1,3-diketo-1,2,3,4,4a,5,6,7-octahydroisoquinoline

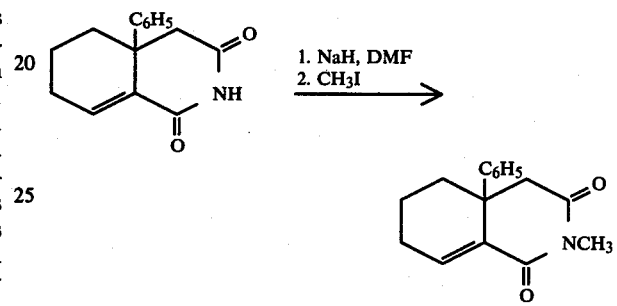

The product of Part B (7.20 g, 29.9 mmoles) in 50 ml of dry dimethylformamide was added to 1.58 g of a 55.5% suspension of sodium hydride in mineral oil (36.5 mmoles NaH), while the reaction mixture was maintained at 70° C. under nitrogen. When evolution of hydrogen ceased (about 1 hour) the reaction mixture was cooled to 25° C. and a solution of methyl iodide (8.52 g, 60 mmoles) in 20 ml of dimethylformamide was added dropwise. The mixture was then heated to 90°–100° C. for 2 hours, after which it was cooled, poured into ice-water and extracted with ether. The ether was evaporated and the residue recrystallized from ethanol to yield 6.56 g (86%) of N-methyl-4a-phenyl-1,3-diketo-1,2,3,4,4a,5,6,7-octahydroisoquinoline.

Anal. Calcd. for $C_{16}H_{17}O_2N$: C, 75.27; H, 6.71; N, 5.49; Found: C, 75.22; H, 6.71; N, 5.71.

Using an analogous procedure but substituting cyclohexylmethyl bromide for methyl iodide, N-cyclohexylmethyl-4a-phenyl-1,3-diketo-1,2,3,4,4a,5,6,7-octahydroisoquinoline was prepared. Similarly, substituting cyclopropylmethyl bromide and cyclobutylmethyl bromide for methyl iodide, N-cyclopropylmethyl-4a-phenyl-1,3-diketo-1,2,3,4,4a,5,6,7-octahydroisoquinoline and N-cyclobutylmethyl-4a-phenyl-1,3-diketo-1,2,3,4,4a,5,6,7-octahydroisoquinoline, respectively, were prepared.

D. N-Methyl-4a-phenyl-1,3-diketo-trans-decahydroisoquinoline

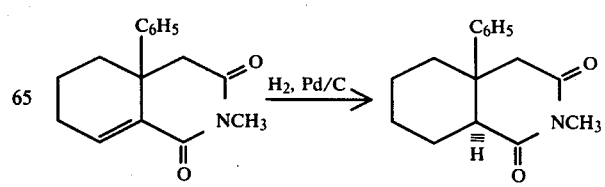

A mixture of the product of Part C (2.0 g, 7.85 mmoles), 175 ml of absolute ethanol, and 300 mg of 5% palladium on carbon was shaken under 40 psi of hydrogen for 24 hours. The catalyst was removed by filtration and the solvent evaporated from the filtrate. Recrystallization of the residue from ethanol gave 1.8 g (90%) of N-methyl-4a-phenyl-1,3-diketo-trans-decahydroisoquinoline, mp 151°-153° C.

Anal. Calcd. for $C_{16}H_{18}NO_2$: C, 74.66; H, 7.44; N, 5.44; Found: C, 74.74; H, 7.66; N, 5.33.

In an analogous procedure reduction of the N-hydrocarbyl-4a-phenyl-1,3-diketo-1,2,3,4,4a,5,6,7-octahydroisoquinolines described in Part C, yielded N-cyclohexylmethyl-4a-phenyl-1,3-diketo-trans-decahydroisoquinoline, N-cyclopropylmethyl-4a-phenyl-1,3-diketo-trans-decahydroisoquinoline and N-cyclobutylmethyl-4a-phenyl-1,3-diketo-trans-decahydroisoquinoline, respectively.

E. N-Methyl-4a-phenyl-1,3-diketo-cis-decahydroisoquinoline

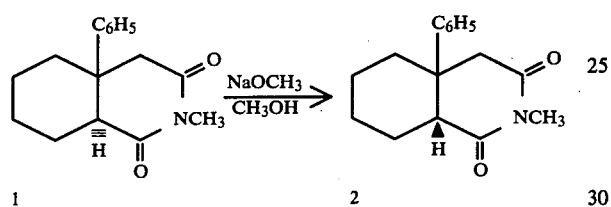

N-Methyl-4a-phenyl-1,3-diketo-trans-decahydroisoquinoline (2.0 g) in 100 ml of methanol was treated with 400 mg of sodium methoxide and the mixture was refluxed for 30 minutes. It was allowed to stand overnight at 25°, then poured into 1 N hydrochloric acid and extracted with ether. The ether extracts were washed successively with water and brine, then dried (MgSO₄) and the ether evaporated to yield 1.9 g of an oil. NMR (CDCl₃): methylene envelope from 70 to 140 cps (8H); singlet at 177 cps (3H); multiplet at 145 to 205 cps (3H); singlet at 434 cps (5H).

A small scale experiment (40 mg compound 1, 1 ml methanol and 10 mg sodium methoxide) conducted in an nmr tube, with spectra being taken at periodic intervals, clearly showed the gradual disappearance of the N-methyl resonance of the starting compound 1 and the appearance of a new N-methyl resonance due to the cis compound. The aromatic proton resonance pattern also underwent a change in the transition from trans to cis conformation. Accordingly, the oil mentioned above was considered to be N-methyl-4a-phenyl-1,3-diketo-cis-decahydroisoquinoline.

F. N-Methyl-4a-phenyl-cis-decahydroisoquinoline

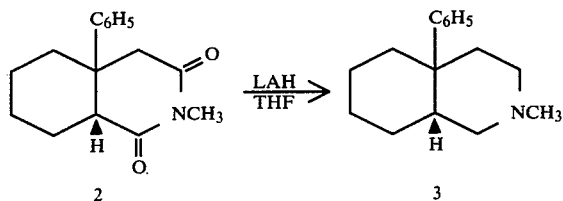

N-Methyl-4a-phenyl-1,3-diketo-cis-decahydroisoquinoline (1.9 g) in 75 ml of anhydrous tetrahydrofuran was treated with lithium aluminum hydride (2.0 g) and refluxed overnight. The reaction was quenched by the successive addition of 2.0 ml of water, 2.0 ml of 15% sodium hydroxide and finally 6.0 ml of water. The inorganic salts were filtered and washed well with ether. The combined filtrates were evaporated to yield 1.6 g of an oil which was evaporatively distilled, bp 125° (0.05 mm), $n_D^{20}$ 1.5514, and identified as N-methyl-4a-phenyl-cis-decahydroisoquinoline.

| Anal. Calcd. for $C_{16}H_{23}N$: | C, 83.77; | H, 10.10; | N, 6.11 |
|---|---|---|---|
| Found: | C, 83.74; | H, 10.11; | N, 6.07. |
| | 83.41 | 10.11 | |

EXAMPLE 2

N-Methyl-4a-(m-methoxyphenyl)-cis-decahydroisoquinoline

A. 2-Cyano-3-carbethoxymethyl-3-(m-methoxyphenyl)cyclohexene

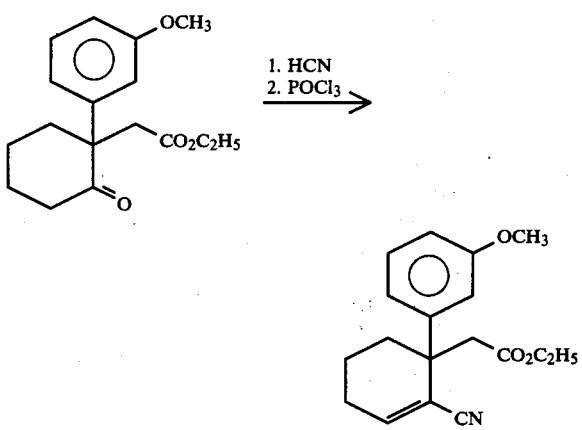

A mixture of 2-carbethoxymethyl-2-(m-methoxyphenyl)cyclohexanone, Langlois et al., Tetrahedron 27, 5641 (1971), (25 g, 86.3 mmoles), 100 ml of hydrogen cyanide and 4 drops of a saturated aqueous potassium cyanide solution was stirred at 0° C. under nitrogen, for 24 hours. After this time, 5 drops of concentrated sulfuric acid was added and the excess hydrogen cyanide evaporated. The residual oil was taken up in ether and washed with 10% aqueous sulfuric acid and then with brine, dried (MgSO₄), and the ether evaporated. The crude cyanohydrin thus obtained was taken up in 175 ml of pyridine, 35 ml of phosphorus oxychloride was added, and the solution was stirred at reflux, under nitrogen, for 3 hours. It was then cooled and poured into a mixture of 500 ml of ice-water and 100 ml of concentrated hydrochloric acid, and the resulting mixture was extracted with ether. After washing the ether extract with brine, drying and concentrating, 22 g of crude product was obtained. This was distilled by short path distillation to yield 16 g, bp 166° C. (0.5 mm). The infrared spectrum of this material indicated it to be 2-cyano-3-carbethoxymethyl-3-(m-methoxyphenyl)cyclohexene with a small amount of an impurity, probably a lactone, with bands at 5.50μ and 5.85μ. The material was considered of sufficient purity to carry it on to the next step.

Anal. Calcd. for $C_{18}H_{21}O_3N$: C, 72.20; H, 7.07; N, 4.68; Found: C, 72.22, H, 7.13; N, 4.10.

B.
4a-(m-Methoxyphenyl)-1,3-diketo-1,2,3,4,4a,5,6,7-octahydroisoquinoline

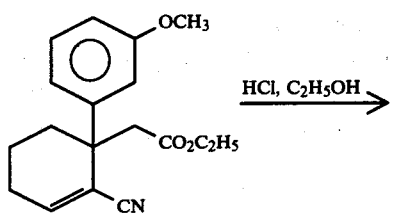

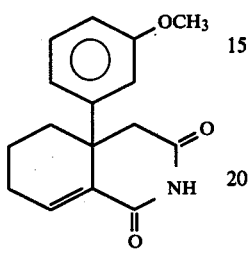

The product of Part A (16 g, 53.5 mmoles) dissolved in absolute ethanol was added to 1.5 liters of absolute ethanol previously saturated with anhydrous hydrogen chloride. The solution was refluxed, under nitrogen, for 48 hours and then allowed to stand at 25° C. for 24 hours. It was concentrated on a rotary evaporator to about 500 ml, cooled in ice, and the resulting crystalline precipitate filtered to yield 8.0 g (55%) of 4a-(m-methoxyphenyl)-1,3-diketo-1,2,3,4,4a,5,6,7-octahydroisoquinoline, mp 230°–232°.

Anal. Calcd. for $C_{16}H_{17}NO_3$: C, 70.83; H, 6.31; N, 5.16; Found: C, 70.97; H, 6.33; N, 5.59.

C.
N-Methyl-4a-(m-methoxyphenyl)-1,3-diketo-1,2,3,4,4a,5,6,7-octahydroisoquinoline

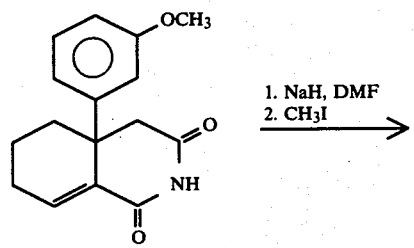

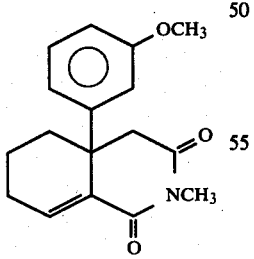

The product of Part B (4.07 g, 15 mmoles) in 50 ml of dry dimethylformamide was added to a mixture of 790 mg of a 55% suspension of sodium hydride (18.1 mmoles of NaH) in mineral oil in 25 ml of dimethylformamide while the temperature of the reaction mixture was maintained at 60°–70° C. under nitrogen. After the addition was complete, the reaction mixture was heated at 90° C. for 2 hours, by which time evolution of hydrogen had ceased. It was then cooled to 30° C. whereupon a solution of 4.25 g (30 mmoles) of methyl iodide in 10 ml of dimethylformamide was added dropwise. The mixture was heated at 90°–100° C. for 2 hours, then cooled, poured into ice-water and extracted with ether. The ether extracts were washed with water, dried (MgSO₄) and evaporated. The residue was recrystallized from ethanol to yield crystalline N-methyl-4a-(m-methoxyphenyl)-1,3-diketo-1,2,3,4,4a,5,6,7-octahydroisoquinoline (3.8 g, 89%), mp 139°–141°.

Anal. Calcd. for $C_{17}H_{18}NO_3$: C, 71.54; H, 6.71; N, 4.91; Found: C, 71.58; H, 6.93; N, 4.94.

D.
N-Methyl-4a-(m-methoxyphenyl)-1,3-diketo-trans-decahydroisoquinoline

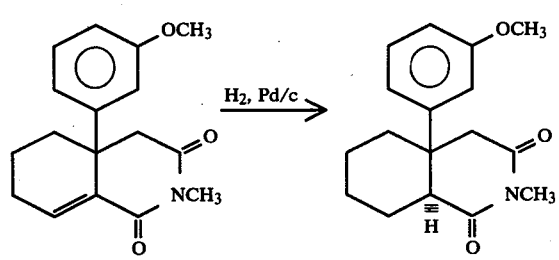

The product of Part C (3.2 g, 11.21 mmoles), 100 ml of glacial acetic acid, 50 ml of dioxane and 700 mg of 5% palladium-on-carbon were shaken under 40 psi of hydrogen for 24 hours. The catalyst was then filtered off and washed well with dioxane, and the combined filtrate was concentrated to a clear oil, yield 3.2 g (99.4%). The product was pure N-methyl-4a-(m-methoxyphenyl)-1,3-diketo-trans-decahydroisoquinoline, as determined by thin-layer chromatography (20% ether-benzene on silica gel plates) and by its nmr spectrum. NMR (CDCl₃): complex multiplet at 50–150 cps from TMS (9H, —CH₂— and

quartet at 148, 163, 173, 189 cps (2H, —CH₂—CO—); singlet at 180 cps (3H, NCH₃); singlet at 220 cps (3H, OCH₃); multiplet at 397–420 cps (4H, Ar-H).

E.
N-Methyl-4a-(m-methoxyphenyl)-1,3-diketo-cis-decahydroisoquinoline

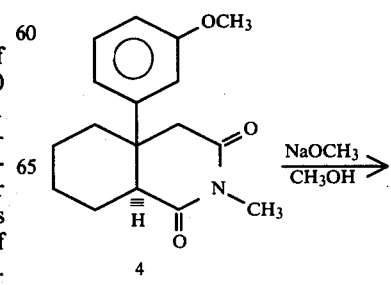

4

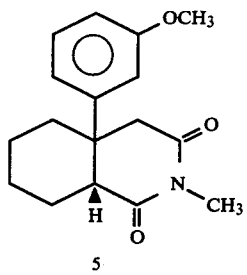

A solution of N-methyl-4a-(m-methoxyphenyl)-1,3-diketo-trans-decahydroisoquinoline (4.6 g, 1.6 mmole) and sodium methoxide (1.84 g, 3.4 mmole) in 150 ml of methanol was stirred at room temperature under nitrogen for 20 hours. It was poured into 150 ml of ice-water and extracted with ether, and the combined extracts were washed with 3 N hydrochloric acid and sat. sodium bicarbonate, dried ($Na_2SO_4$) and evaporated. The crude product was a white viscous oil (3.8 g). Thin layer chromatography on silica gel, eluting with 10% ether/benzene, showed a major spot ($R_f$ 0.31) and a minor component ($R_f$ 0.07). The major component, N-methyl-4a-(m-methoxyphenyl)-1,3-diketo-cis-decahydroisoquinoline, was clearly separated by preparative thick layer chromatography and isolated as a colorless oil.

NMR: 7.2 (q, J=8, 1H, Ar-H), 7.0-6.65 (m's, 3H, Ar-H), 3.76 (s, 3H, —$OCH_3$), 3.0 (s, 3H, $NCH_3$), 3.15-2.95 (m, 2H, —$CH_2CO$—), 3.4-3.2 (br, m, 1H, $$-\overset{|}{\underset{}{C}}H-)$$

2.2-1.4 (m's, 8H —$CH_2$—).

F.
N-Methyl-4a-(m-methoxyphenyl)-cis-decahydroisoquinoline

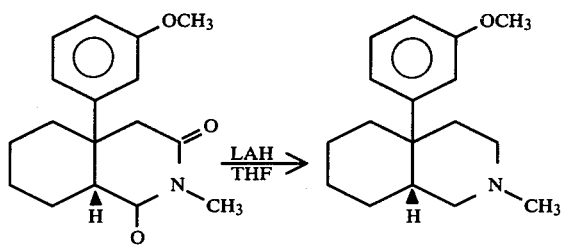

$R^1 = CH_3$
$R^2 = H_2$
$Ar = C_6H_4OCH_3$

A solution of N-methyl-4a-(m-methoxyphenyl)-1,3-diketo-cis-decahydroisoquinoline (3.8 g, 1.3 mmoles) in 50 ml of dry tetrahydrofuran was added dropwise to a stirred suspension of 3.8 g of lithium aluminum hydride in 25 ml of tetrahydrofuran under nitrogen. When addition was complete, the reaction mixture was refluxed overnight, then cooled and excess hydride destroyed by dropwise addition of 3.8 ml of water, 3.8 ml of 3 N sodium hydroxide and 11.4 ml of water. The resultant white salts were filtered off and washed with ether. The organic solution was dried ($Na_2SO_4$) and evaporated, leaving 2.5 g of an opaque oil. This was evaporatively distilled at 50° at 0.3 microns Hg. The product was isolated as a colorless, viscous oil identified as N-methyl-4a-(m-methoxyphenyl)-cis-decahydroisoquinoline, yield 2.38 g. HRMS: Calc. MW for $C_{17}H_{25}NO$: 259.1935 Measured: 259.1936 NMR: 7.27 (t, J=8, 1H, Ar-H), 7.18-6.95 (m's, 2H, Ar-H), 6.73 (d×t, J=7.5, 2, 1H, Ar-H), 3.78 (s, 3H, —$OCH_3$), 2.6-2.3 (sh, m, 4H, —$CH_2$—), 2.23 (s, 3H, —$NCH_3$), 2.0-1.2 (m, 11H, —$CH_2$, $$-\overset{|}{\underset{}{C}}H-).$$

EXAMPLE 3

N-(4-Phenyl-n-butyl)-4a-(m-methoxyphenyl)-cis-decahydroisoquinoline

A.
N-(4-Phenyl-n-butyl)-4a-(m-methoxyphenyl)-1,3-diketo-cis-decahydroisoquinoline

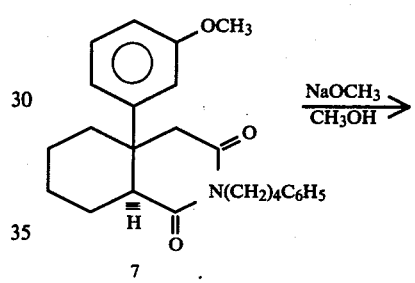

7

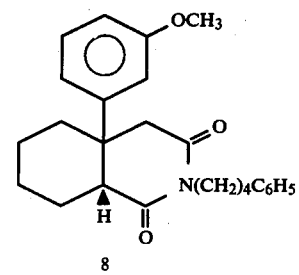

8

N-(4-Phenyl-n-butyl)-4a-(m-methoxyphenyl)-1,3-diketo-trans-decahydroisoquinoline (7) was prepared by substituting phenylbutyl bromide for the methyl iodide of step C of Example 2 and proceeding as in the subsequent steps of Example 2. 1.1 gram of the resultant compound (7) in 50 ml of methanol was treated with 400 mg of sodium methoxide and the solution stirred at 25° for 72 hours. It was then poured into water and extracted with ether. The organic extracts were washed successively with water, 3 N hydrochloric acid, saturated sodium bicarbonate and brine, and finally dried over anhydrous sodium sulfate. Evaporation of the ether gave 0.81 g of a clear oil whose nmr and ir spectra, being distinct from the trans starting material, identified it as the cis isomer. Thin-layer chromatography (silica gel, 10% ether-benzene) showed a single spot.

B.
N-(4-Phenyl-n-butyl)-4a-(m-methoxyphenyl)-cis-decahydroisoquinoline

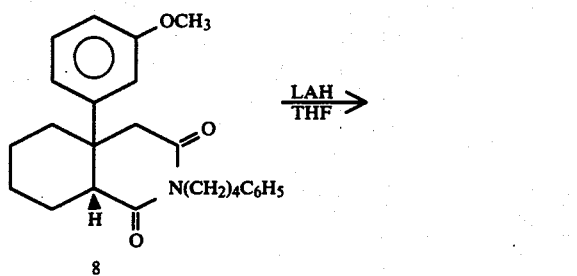

$R^1$ = (CH$_2$)$_4$C$_6$H$_5$
$R^2$ = H$_2$
Ar = C$_6$H$_4$OCH$_3$

N-(4-Phenyl-n-butyl)-4a-(m-methoxyphenyl)-1,3-diketo-cis-decahydroisoquinoline (0.8 g) in anhydrous tetrahydrofuran was treated with 0.8 g of lithium aluminum hydride and refluxed overnight. The reaction mixture was worked up as indicated in Example 2-B to yield 0.7 g of an opaque oil which was evaporatively distilled, bp 80°–90°, and identified as N-(4-phenyl-n-butyl)-4a-(m-methoxyphenyl)-cis-decahydroisoquinoline.

EXAMPLE 4
N-Phenethyl-4a-phenyl-cis-decahydroisoquinoline
A.
N-Phenethyl-4a-phenyl-1,3-diketo-cis-decahydroisoquinoline

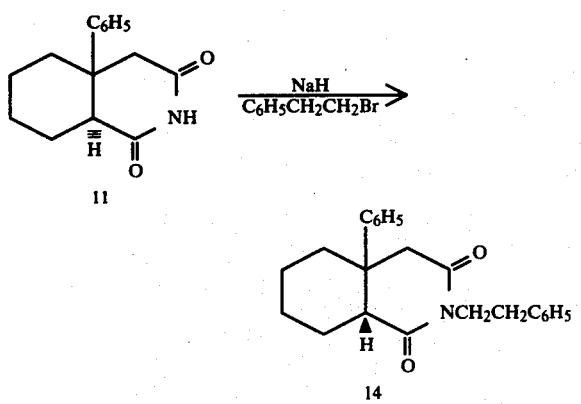

A solution of 4a-phenyl-1,3-diketo-trans-decahydrosoquinoline (2.0 g, 8.22 mmoles) from Ex. 6A in 35 ml of dry dimethylformamide was added dropwise to 375 mg of a 55% suspension of sodium hydride in mineral oil in 15 ml of dimethylformamide at 70° C. The reaction mixture was heated at 70° C. until hydrogen evolution ceased. It was then cooled to 10° C. and a solution of 1.52 g (8.22 mmoles) of phenethyl bromide in 20 ml of dimethylformamide was added. The mixture was stirred for 24 hours at 25° C., then poured into water and extracted with ether. The resulting crude product from the ether extracts was chromatographed on 100 g of Florisil and eluted with 4% acetone-hexane to yield 1.8 g (63.5%) of a clear oil, which was identified by nmr as N-phenethyl-4a-phenyl-1,3-diketo-cis-decahydroisoquinoline.

NMR (CDCl$_3$): Complex multiplet at 80 to 140 cps from TMS (methylene H, 9H); complex multiplet at 140 to 200 cps (4H, —CH$_2$CO and —CH$_2\phi$); multiplet at 220 to 243cps (2H, NCH$_2$); multiplets at 420 to 445 cps (10H, ArH).

B. N-Phenethyl-4a-phenyl-cis-decahydroisoquinoline

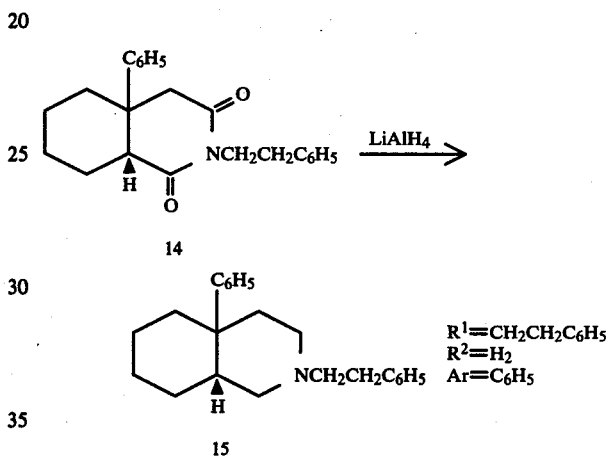

$R^1$=CH$_2$CH$_2$C$_6$H$_5$
$R^2$=H$_2$
Ar=C$_6$H$_5$

The product of Part A (1.8 g, 5.19 mmoles) in 50 ml of sodium-dried tetrahydrofuran was treated with 2.0 g of lithium aluminum hydride, under nitrogen, and the mixture was stirred and refluxed for 24 hours. It was allowed to cool, then was treated successively with 2.0 ml of water, 2.0 ml of 15% aqueous sodium hydroxide and 6.0 ml of water. The precipitated inorganic salts were filtered off and washed well with ether. The combined filtrates were dried over anhydrous potassium carbonate and concentrated to an oil. Evaporative distillation gave 1.4 g (87.5%) of N-phenethyl-4a-phenyl-cis-decahydroisoquinoline as a clear oil, bp 160° C. (0.002 mm).

Anal. Calcd. for C$_{23}$H$_{29}$N: C, 86.44; H, 9.15; N, 4.39; Found: C, 86.00; H, 9.11; N, 3.86.

In place of phenethyl bromide in the preceding (Part A), p-bromophenethyl bromide, m-chlorophenethyl bromide, o-fluorophenethyl bromide, p-trifluoromethylphenethyl bromide, 2,4-dimethoxyphenethyl bromide, 3,4-methylenedioxyphenethyl bromide, and 3,4-dichlorophenethyl bromide or corresponding mesylates can be employed to give the corresponding N-substituted-phenethyl-4a-phenyl-cis-decahydroisoquinoline.

EXAMPLE 5

N-Cyclopropylmethyl-4a-(m-methoxyphenyl)-cis-decahydroisoquinoline

A.
N-Cyclopropylmethyl-4a-(m-methoxyphenyl)-1,3-diketo-cis-decahydroisoquinoline

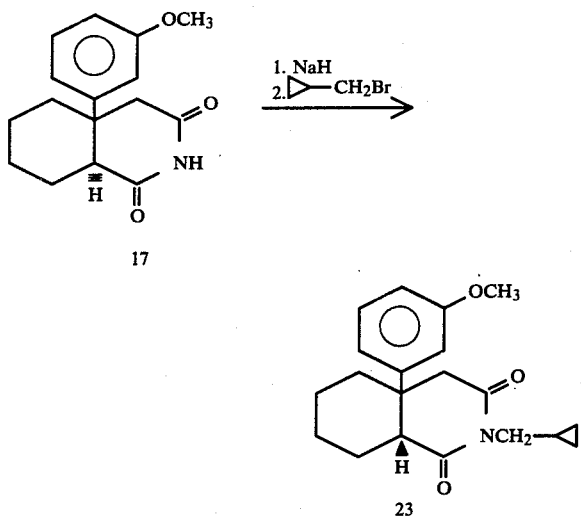

A solution of 2.0 g (7.3 mmoles) of 4a-(m-methoxyphenyl)-1,3-diketo-trans-decahydroisoquinoline (Ex. 7A) in 50 ml of anhydrous dimethylformamide was added to 35.1 mg of a 55% suspension of sodium hydride in mineral oil in 25 ml of dimethylformamide heated at 70°. Heating was continued for 45 minutes after the addition was complete after which time 1.09 g (8.1 mmoles) of cyclopropylmethyl bromide in 10 ml of dimethylformamide was added. The reaction mixture was heated at 80° for 2 hours and allowed to stand at 25° overnight. It was poured into water and extracted with ether. Evaporation of the ether gave an oil which showed one spot by thin-layer chromatography (silica gel plates, benzene solvent, $R_f$ 0.4, starting material had $R_f$ 0.07) and was identified by nmr as N-cyclopropylmethyl-4a(m-methoxyphenyl)-1,3-diketo-cis-decahydroisoquinoline.

NMR (CDCl$_3$): multiplet at 5 to 22 cps (4H); methylene envelope at 40-130 cps (9H); multiplets from 150-220 cps (5H); singlet at 227 cps (3H); multiplets at 400-445 cps (4H).

B.
N-Cyclopropylmethyl-4a-(m-methoxyphenyl)-cis-decahydroisoquinoline

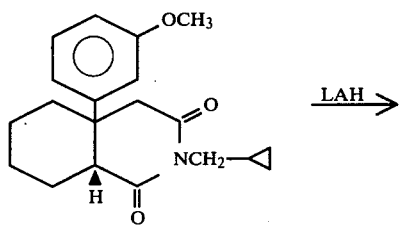

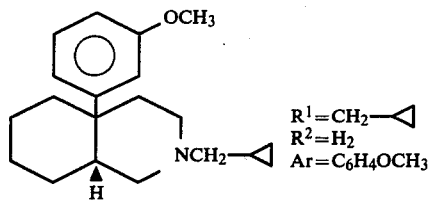

The product of Part A (2.17 g, 6.6 mmoles) in 75 ml of sodium-dried tetrahydrofuran was treated with 2.2 g (58 mmoles) of lithium aluminum hydride, under nitrogen, and the mixture was stirred and refluxed for 24 hours. It was then treated successively with 2.2 ml of water, 2.2 ml of 15% sodium hydroxide and 6.6 ml of water. The inorganic salts were filtered and washed well with ether. The combined filtrates were evaporated and the residual N-cyclopropylmethyl-4a-(m-methoxyphenyl)-cis-decahydroisoquinoline (oil) evaporatively distilled, bp 125° (0.005 mm).

NMR (CDCl$_3$): methylene envelope at 5 to 160 cps from TMS (22H); singlet at 228 cps (3H); multiplets from 398 to 445 cps (4H).

EXAMPLE 6

N-Allyl-4a-phenyl-trans-decahydroisoquinoline

A. 4a-Phenyl-1,3-diketo-trans-decahydroisoquinoline

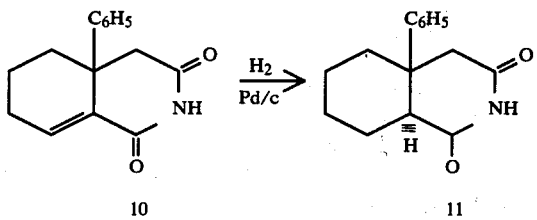

4a-Phenyl-1,3-diketo-1,2,3,4,4a,5,6,7-octahydroisoquinoline (3.0 g, 12.45 mmoles) from Ex. 1B was dissolved in 100 ml of glacial acetic acid and 50 ml of dioxane. The catalyst, 5% palladium on carbon (700 mg), was added and the mixture was hydrogenated under 40 psi of hydrogen for 24 hours in a Parr shaker. The catalyst was then filtered off and the filtrate evaporated. The white crystalline 4a-phenyl-1,3-diketo-trans-decahydroisoquinoline was recrystallized from ethanol, mp 180°-182.5°.

Anal. Calcd. for C$_{15}$H$_{17}$NO$_2$: C, 74.05; H, 7.04; N, 5.75; Found: C, 74.30; H, 7.22; N, 5.55.

B.
N-Allyl-4a-phenyl-1,3-diketo-cis-decahydroisoquinoline

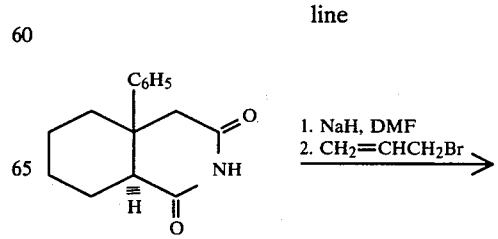

-continued

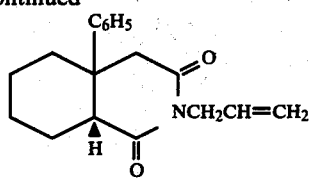

12

A solution of the product of Part A above (2.0 g; 8.23 mmoles) in 35 ml of dry dimethylformamide was added dropwise to 440 mg of a 55% suspension of sodium hydride in mineral oil in 15 ml of dimethylformamide at 70° C. The reaction mixture was heated at 70° C. until hydrogen evolution ceased (ca 1 hour). It was then cooled to 25° C. and a solution of 1.01 g (8.35 mmoles) of allyl bromide in 15 ml of dimethylformamide was added. The mixture was heated at 90°–100° C. for 2 hours, then cooled and poured into ice-water. Extraction with ether gave, after drying (K$_2$CO$_3$) and evaporation of the ether, 2.5 g of crude product (oil). This material was chromatographed on 100 g of Florisil and eluted with 3–5% acetone-hexane to give 1.7 g (oil) of N-allyl-4a-phenyl-1,3-diketo-cis-decahydroisoquinoline, shown to be pure by thin-layer chromatography (20% ether-benzene with silica gel plates).

In an analogous procedure, when propargyl bromide was substituted for allyl bromide, N-propargyl-4a-phenyl-1,3-diketo-cis-decahydroisoquinoline was obtained.

C. N-Allyl-4a-phenyl-cis-decahydroisoquinoline

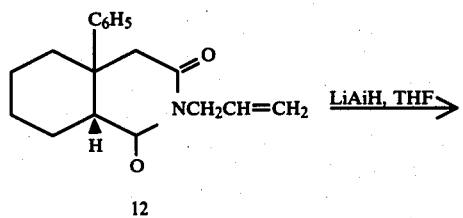

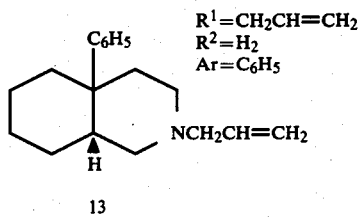

The product of Part B (1.7 g, 6.0 mmoles) in 50 ml of sodium-dried tetrahydrofuran was treated with 1.7 g (44.7 mmoles) of lithium hydride, under nitrogen, and the mixture was stirred and refluxed for 24 hours. It was allowed to cool and then was treated successively with 1.7 ml of water, 1.7 ml of 15% aqueous sodium hydroxide and 5.1 ml of water. The precipitated inorganic salts were filtered off and washed well with ether. The combined filtrates were dried over anhydrous potassium carbonate and concentrated to an oil. Evaporative distillation gave 1.0 g (65.5%) of N-allyl-4a-phenyl-cis-decahydroisoquinoline as a clear oil, bp 117° C. (0.07 mm).

Anal. Calcd. for C$_{18}$H$_{25}$N: C, 84.67; H, 9.86; N, 5.48; Found: C, 84.30; H, 9.79; N, 5.11.

Similarly, lithium aluminum hydride reduction of N-propargyl-4a-phenyl-1,3-diketo-cis-decahydroisoquinoline yielded N-propargyl-4a-phenyl-cis-decahydroisoquinoline.

EXAMPLE 7

N-allyl-4a-(m-methoxyphenyl)-cis-decahydroisoquinoline

A.
4a-(M-Methoxyphenyl)-1,3-diketo-trans-decahydroisoquinoline

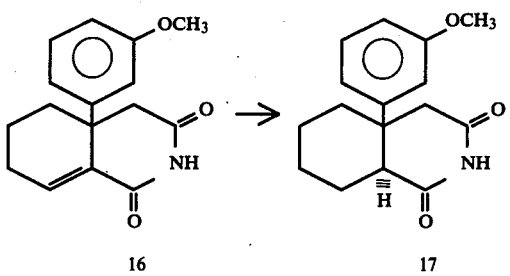

A solution of 4a-(m-methoxyphenyl)-1,3-diketo-1,2,3,4,4a,5,6,7-octahydroisoquinoline (6.0 g) in 250 ml of glacial acetic acid was treated with 1 g of 5% palladium on carbon and the mixture hydrogenated under 40 psi of hydrogen for 24 hours in a Parr shaker. The catalyst was then filtered off and the filtrate evaporated. The residual 4a-(m-methoxyphenyl)-1,3-diketo-trans-decahydroisoquinoline was recrystallized from ethanol, m.p. 189–190.

| Anal. Calcd. for C$_{16}$H$_{19}$NO$_3$: | C, 70.31; | H, 7.01; | N, 5.12 |
|---|---|---|---|
| Found: | C, 70.60; | H, 7.01; | N, 5.05 |
|  | 70.46 | 7.02 | 5.13 |

B.
N-Allyl-4a-(m-methoxyphenyl)-cis-1,3-diketodecahydroisoquinoline

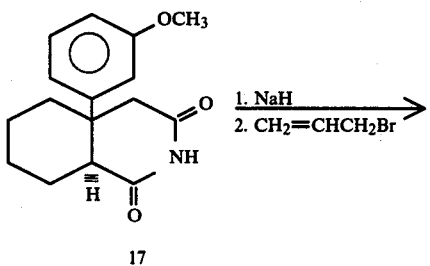

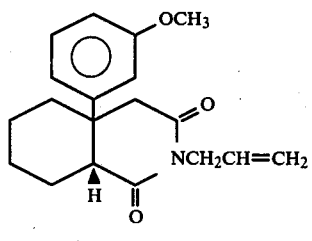

18

The product of Part A (4.5 g, 16.5 mmoles) in 70 ml of dry dimethylformamide was added dropwise to 880 mg of a 55% suspension of sodium hydride in mineral oil in 30 ml of dimethylformamide at 70°–80°. The mixture was heated at 70° and stirred for 1 hour. It was then cooled to 35°, whereupon allyl bromide (2.02 g, 16.7 mmoles) in 30 ml of dimethylformamide was added dropwise. After heating the reaction mixture at 90°–110° for 2 hours and allowing it to stand at 25° overnight it was poured into ice-cold 1% hydrochloric acid and extracted with ether. The organic extracts were washed with water, brine, then dried (magnesium sulfate). Evaporation of the ether yielded 5.6 g of crude product which was chromatographed on 200 g of Florisil and eluted with 5% acetone-hexane to yield 4.0 g of N-allyl-4a-(m-methoxyphenyl)-cis-1,3-diketodecahydroisoquinoline (oil), which was evaporatively distilled, bp 160° (0.05 mm).

| Anal. Calcd. for $C_{19}H_{23}O_3N$: | C, 72.81; | H, 7.40; | N, 4.47 |
|---|---|---|---|
| Found: | C, 72.62; | H, 7.50; | N, 4.48 |
| | 72.46 | 7.37 | |

Treatment of a sample of the allyl derivative prepared as above with sodium methoxide in methanol (both at room temperature and reflux) or with potassium t-butoxide in THF left it totally unchanged, confirming that the cis derivative has been formed initially. Also confirmed by spectral analysis. NMR: 7.2 (q, J=8, 1H, Ar-H), 7.05-6.75 (m, 3H, Ar-H), 5.9-5.3 (m, 1H, —CH=), 5.1-4.5 (m, 2H, =CH$_2$), 4.4–4.15 (m, 2H, n-CH$_2$-), 3.75 (s, 3H, —OCH$_3$), 3.4-2.6 (m's, 3H, —CH$_2$CO and $$-\overset{|}{C}HCO),$$

2.1-1.4 (m, 8H, —CH$_2$—).

C. N-allyl-4a-(m-methoxyphenyl)-cis-decahydroisoquinoline

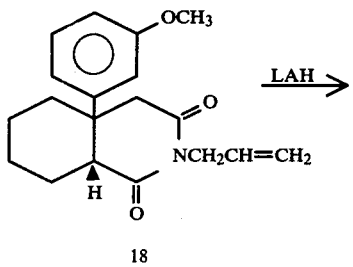

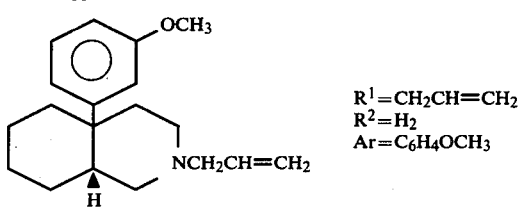

The product of Part B (4.0 g, 12.8 mmoles) in 75 ml of sodium-dried tetrahydrofuran was treated with 4.0 g (105 mmoles) of lithium aluminum hydride, under nitrogen, and the mixture was stirred and refluxed for 24 hours. It was allowed to cool and then treated successively with 4.0 ml of water, 4.0 ml of 15% aqueous sodium hydroxide, and finally with 12.0 ml of water. The precipitated inorganic salts were filtered off and washed well with ether. The combined filtrates were dried over anhydrous potassium carbonate to yield, after evaporation of the ether, 3.27 g of N-allyl-4a-(m-methoxyphenyl)-cis-decahydroisoquinoline (oil), which was evaporatively distilled, bp 150° (0.05 mm).

NMR (CDCl$_3$): complex multiplet at 70 to 190 cps from TMS (methylene H, 17H); singlet at 234 cps (3H, OCH$_3$); multiplets at 300–350 cps (vinyl H) and multiplets at 405 to 460 cps (aromatic H).

IR: 6.10μ (C=C); 6.25, 6.35μ (Ar).

EXAMPLE 8

N-Allyl-4a-(m-hydroxyphenyl)-cis-decahydroisoquinoline

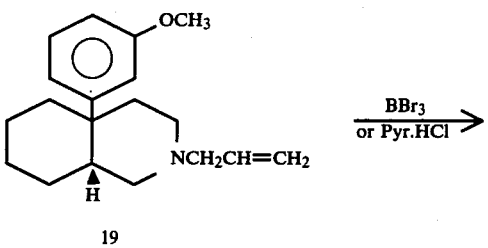

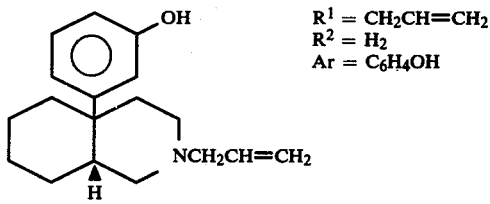

A. A solution of 880 mg (3.09 mmoles) of N-allyl-4a-(m-methoxyphenyl)-cis-decahydroisoquinoline in 30 ml of methylene chloride was added in portions to an ice-cold solution of 0.6 ml of boron tribromide in 15 ml of methylene chloride. The reaction mixture was stirred at 0° for 5 hours, then overnight at 25°. Methanol (5 ml) was added and the solution was evaporated under vacuum. The residue was treated with 15 ml of 5 N sodium hydroxide and stirred for 15 minutes. Ether (50 ml) was added and, after stirring for 2 hours, the layers were separated and the aqueous portion, after being further extracted with ether, was then saturated with carbon dioxide. The resulting mixture was extracted with ether and the ether extracts were washed with brine, then dried (K$_2$CO$_3$) and evaporated to yield 370 mg of a white foam. NMR spectra confirmed the loss of the O-methyl, identifying the product as N-allyl-4a-(m-hydroxyphenyl)-cis-decahydroisoquinoline. NMR: methylene envelope at 60–200 cps from TMS (17H); multiplets at 300–330 cps, singlet at 341 cps, multiplet at 395-450 cps.

B. N-Allyl-4a-(m-methoxyphenyl)-cis-decahydroisoquinoline (900 mg) and pyridine hydrochloride (5 g) were mixed and heated at 200°, under nitrogen, for 1 hour. The reaction was cooled and diluted with water, then extracted with ether. The aqueous portion was basified with potassium carbonate and extracted with ether. This ether extract was concentrated and the residue evaporatively distilled, bp, 250° (2 microns); yield, 380 mg.

Mass. Spec.: Calcd for C$_{18}$H$_{25}$NO: 271.1935: Found: 271.1884.

EXAMPLE 9

N-(3,3-Dimethylallyl)-4a-(m-methoxyphenyl)-cis-decahydroisoquinoline

A.
N-(3,3-Dimethylallyl)-4a-(m-methoxyphenyl)-1,3-diketo-cis-decahydroisoquinoline

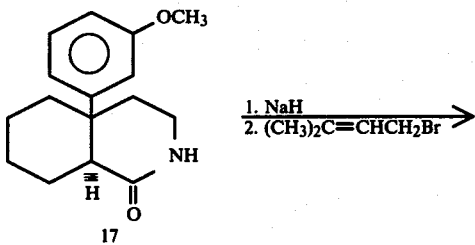

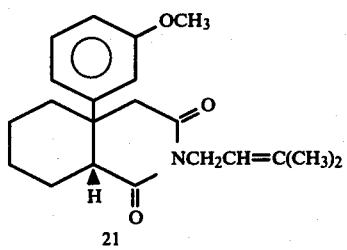

A solution of 4 g (14.7 mmoles) of 4a-(m-methoxyphenyl)-1,3-diketo-trans-decahydroisoquinoline in 50 ml of anhydrous dimethylformamide was added dropwise to 700 mg of a 55% suspension of sodium hydride in mineral oil in 50 ml of dimethylformamide at 70°. The reaction mixture was heated for 1 hour after the addition was complete and then cooled to 25°. 3,3-Dimethylallyl bromide (2.37 g, 15.8 mmoles) in 10 ml of dimethylformamide was added dropwise and the solution stirred overnight at 25°. After heating at 80° for 1 hour it was poured into water and extracted with ether to yield 4.74 g of N-(3,3-dimethylallyl)-4a-(m-methoxyphenyl)-1,3-diketo-cis-decahydroisoquinoline (oil), which was evaporatively distilled, bp 225° (0.005 mm).

Anal. Calcd. for $C_{21}H_{27}O_3N$: C, 73.86; H, 7.97; N, 4.10
Found: C, 74.48; H, 7.25; N, 4.07
       74.40      7.88

B.
N-(3,3-Dimethylallyl)-4a-(m-methoxyphenyl)-cis-decahydroisoquinoline

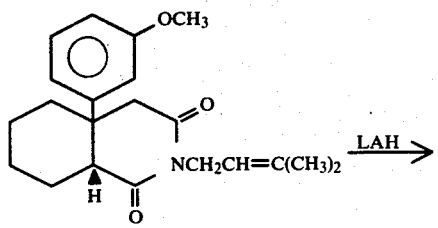

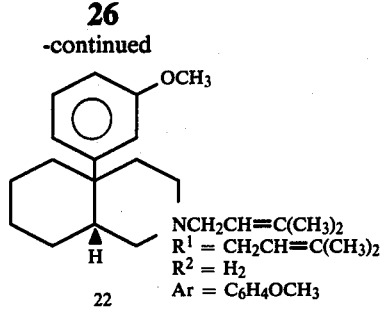

A solution of 4.5 g (13.2 mmoles) of the product of Part A in 100 ml of sodium-dried tetrahydrofuran was treated with 4.5 g of lithium aluminum hydride and the mixture refluxed overnight. The reaction was quenched by adding, successively, 4.5 ml of water, 4.5 ml of 15% sodium hydroxide and finally 14.5 ml of water. The inorganic salts were filtered and the filtrate evaporated on a rotary evaporator to yield N-(3,3-dimethylallyl)-4a-(m-methoxyphenyl)-cis-decahydroisoquinoline (oil), which was evaporatively distilled, bp 125° (0.005 mm).

Anal. Calcd. for $C_{21}H_{31}NO$: C, 80.45; H, 9.97; N, 4.47
Found: C, 80.51; H, 10.31; N, 4.56
       80.26     10.41      4.72

EXAMPLE 10

N-Cyclopropylmethyl-4a-(m-hydroxyphenyl)-cis-decahydroisoquinoline

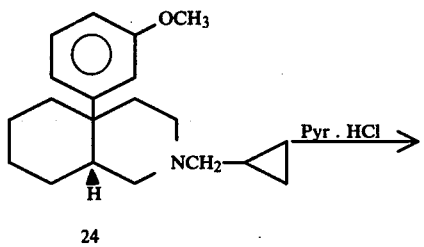

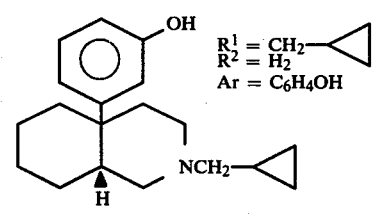

N-Cyclopropylmethyl-4a-(m-methoxyphenyl)-cis-decahydroisoquinoline (1.52 g, 5.1 mmoles) and pyridine hydrochloride (3.0 g, 26 mmoles) were mixed and heated with stirring under nitrogen at 190° for 1 hour. When cooled, the mixture solidified and was dissolved in water and extracted with ether. The aqueous solution was basified to pH 8 with potassium carbonate and again extracted with ether. The combined extracts were dried ($Na_2SO_4$) and evaporated, yielding 0.6 g of starting material. The aqueous layer was made strongly basic by adding additional potassium carbonate and again extracted with ether, and the extracts dried ($Na_2SO_4$) and evaporated. The residue was evaporatively distilled, yielding starting material (bp, 70° at 0.002 mm)

and N-cyclopropylmethyl-4a-(m-hydroxyphenyl)-cis-decahydroisoquinoline (bp, 80° at 0.002 mm), which formed a glass when cooled.

NMR (CDCl₃): 7.3-6.85 (m, 3H), 6.8-6.5 (m, 1H), 2.9-2.1 (m, 7H), 2.1-1.1 (m, 10H), 1.1-0.0 (m, 5H).

EXAMPLE 11

N-Cyclobutylmethyl-4a-(m-methoxyphenyl)-cis-decahydroisoquinoline

A.

N-Cyclobutylmethyl-4a-(m-methoxyphenyl)-1,3-diketo-cis-decahydroisoquinoline

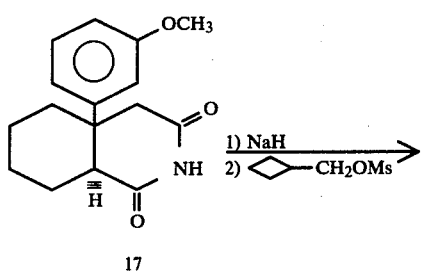

17

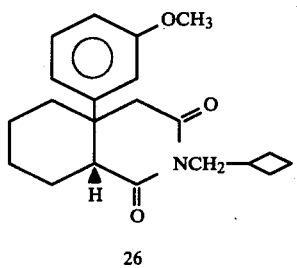

26

A solution of 5.0 g (18.5 mmoles) of 4a-(m-methoxyphenyl)-1,3-diketo-trans-decahydroisoquinoline in 125 ml of anhydrous dimethylformamide was added to a suspension of 1.35 g (28 mmoles) of 50% sodium hydride in mineral oil (washed with pentane) in 60 ml of anhydrous dimethylformamide heated at 50° under nitrogen. The mixture was heated at 90° for 2 hours, then cooled to 40°. A solution of 6.05 g (37 mmoles) of freshly prepared cyclobutylmethyl mesylate (prepared according to the procedure of Crossland and Servis, J. Org. Chem. 35, 3195 (1970)) in 10 ml of anhydrous dimethylformamide was added and the reaction mixture heated at 90° overnight. It was then cooled and poured into ice-water and extracted with ether. Evaporation of the ether gave an oil, identified as N-cyclobutylmethyl-4a-(m-methoxyphenyl)-1,3-diketo-cis-decahydroisoquinoline.

NMR (CDCl₃): 7.4-6.6 (m, 4H); 4.3-3.7 (m, 2H); 3.8 (s, 3H); 3.1-2.8 (m, 2H); 2.4-1.2 (m, 16H).

B.

N-Cyclobutylmethyl-4a-(m-methoxyphenyl)-cis-decahydroisoquinoline

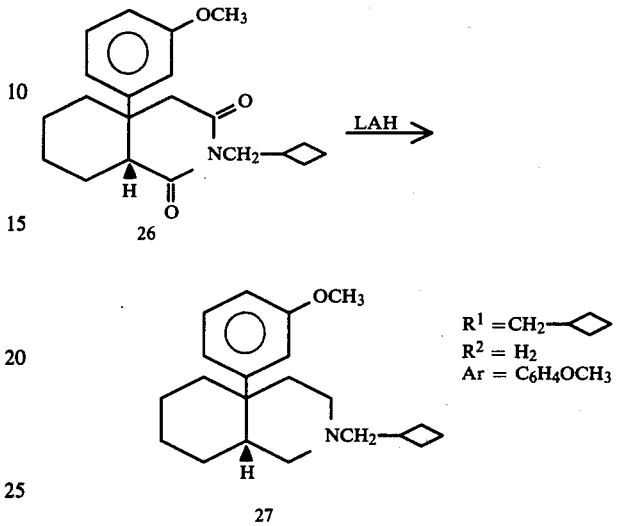

The product of Part A (3.9 g, 11.4 mmoles) in 300 ml of sodium-dried tetrahydrofuran was added with stirring to a suspension of 4.0 g of lithium aluminum hydride in 100 ml of tetrahydrofuran under nitrogen, and the mixture was stirred at reflux for 20 hours. It was then cooled and treated successively with 4.0 ml of water, 4.0 ml of 3 N sodium hydroxide and 12.0 ml of water. The inorganic salts were filtered and washed with ether. The combined filtrates were evaporated, and the residual N-cyclobutylmethyl-4a-(m-methoxyphenyl)-cis-decahydroisoquinoline (oil), was purified by Preparative Thick Layer Chromatography (silica gel, ethyl acetate/methanol 99:1) and evaporative distillation, bp 70° (0.001 mm).

NMR (CDCl₃): 7.4-6.6 (m, 4H); 3.8 (s, 3H); 2.7-2.2 (m, 8H); 2.2-1.2 (m, 16H).

Mass Spec.: Calcd for C₂₁H₃₁NO: 313.2404; Found: 313.2362.

EXAMPLE 12

N-Phenethyl-4a-(m-methoxyphenyl)-cis-decahydroisoquinoline

A.

N-Phenethyl-4a-(m-methoxyphenyl)-1,3-diketo-cis-decahydroisoquinoline

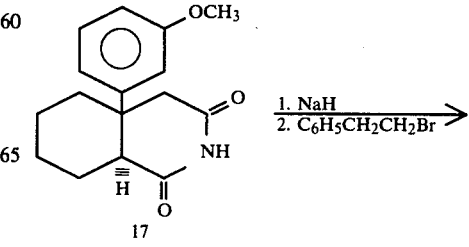

17

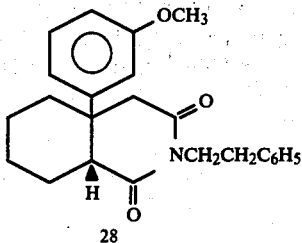

28

A solution of 10.0 g (37 mmoles) of 4a-(m-methoxyphenyl)-1,3-diketo-trans-decahydroisoquinoline in 250 ml of anhydrous dimethylformamide was added with stirring to a suspension of 2.8 g (55.5 mmoles) of 50% sodium hydride in mineral oil (washed with pentane) in 125 ml of anhydrous dimethylformamide heated at 50° under nitrogen. The mixture was heated at 90° for 2 hours, then cooled to 40°, at which time a solution of 14.0 g (74 mmoles) of phenethyl bromide in 20 ml of anhydrous dimethylformamide was added and the reaction mixture heated at 90° overnight. The cooled solution was poured into ice-water and extracted with ether. Evaporation of the ether gave an oil which was purified by column chromatography (Silicar CC-7, eluting with acetone-benzene). The major fraction was identified as N-phenethyl-4a-(m-methoxyphenyl)-1,3-diketo-cis-decahydroisoquinoline.

NMR (CDCl$_3$): 7.2-7.0 (m 6H); 6.95-6.6 (m, 3H); 4.0-3.7 (m, 2H); 3.75 (s, 3H), 3.2-2.8 (m, 3H); 2.8-2.35 (m, 2H), 2.0-1.3 (m, 8H).

B.
N-Phenethyl-(m-methoxyphenyl)-cis-decahydroisoquinoline

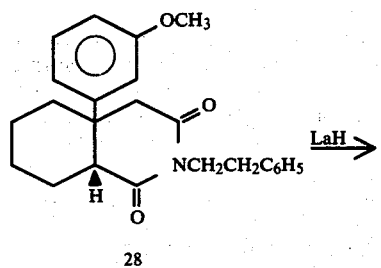

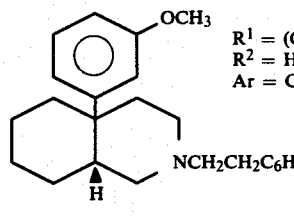

29

The product of Part A (5.0 g, 13.3 mmoles) in 200 ml of sodium-dried tetrahydrofuran was added to a stirred suspension of 5.0 g of lithium aluminum hydride in 80 ml of tetrahydrofuran under nitrogen, and the mixture was stirred at reflux for 20 hours. It was cooled and treated successively with 5.0 ml of water, 5.0 ml of 3N sodium hydroxide and 15.0 ml of water. The inorganic salts were filtered and washed with ether. The combined filtrates were evaporated and the residual N-phenethyl-4a-(m-methoxyphenyl)-cis-decahy-droisoquinoline (oil) was evaporatively distilled, bp 70° (0.002 mm).

NMR (CDCl$_3$): 7.21 (s, 5H); 7.3-6.88 (m, 3H); 6.8-6.55 (m, 1H); 3.79 (s, 3H); 2.9-2.3 (m, 8H); 2.1-1.1 (m, 11H).

| Anal. Calcd. for C$_{24}$H$_{31}$NO: | C, 82.47; | H, 8.94; | N, 4.01 |
|---|---|---|---|
| Found: | C, 82.21; | H, 9.06; | N, 3.96 |
| | 82.25 | 9.04 | 3.98. |

EXAMPLE 13

N-Phenethyl-4a-(m-hydroxyphenyl)-cis-decahydroisoquinoline

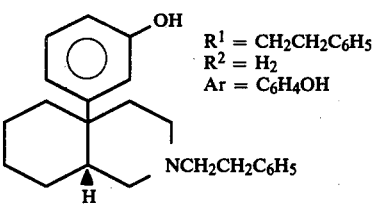

29

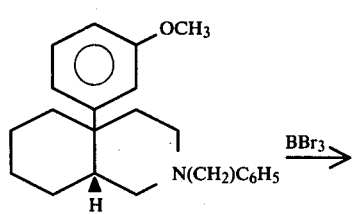

$R^1$ = CH$_2$CH$_2$C$_6$H$_5$
$R^2$ = H$_2$
Ar = C$_6$H$_4$OH

30

N-Phenethyl-4a-(m-methoxyphenyl)-cis-decahydroisoquinoline (1.49 g, 4.28 mmoles) was mixed with pyridine hydrochloride (3.0 g, 25.8 mmoles) and stirred under nitrogen for 1 hour while heating at 190°. After cooling the solid mixture was dissolved in chloroform, and the chloroform solution was washed with water, dried (Na$_2$SO$_4$) and evaporated. The residue was evaporatively distilled, bp 95° (0.0002 mm), yielding a glass (mp 70°-80°) which was identified as N-phenethyl-4a-(m-hydroxyphenyl)-cis-decahydroisoquinoline, hydrochloride salt.

NMR (CDCl$_3$): 7.17 (s, 5H),; 7.3-6.6 (m, 4H); 3.1-2.5 (m, 9H); 2.3-1.2 (m, 10H).

EXAMPLE 14

N-(4-Phenyl-n-butyl)-4a-(m-hydroxyphenyl)-cis-decahydroisoquinoline

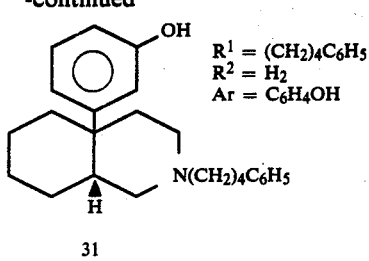

A solution of 0.88 g (2.34 mmoles) of N-(4-phenyl-n-butyl)-4a-(m-methoxyphenyl)-cis-decahydroisoquinoline in 100 ml of methylene chloride was added with stirring to a solution of 0.45 ml (4.68 mmoles) of boron tribromide in 50 ml of methylene chloride at −78° under nitrogen. After 1 hour, 10 ml of methanol was added and the methylene chloride was removed under vacuum. The residue was treated with 40 ml of 6N sodium hydroxide and then stirred as a two-phase system with 100 ml of ether. The residue from the ether extract was evaporatively distilled, and the glass obtained was identified as N-(4-phenyl-n-butyl)-4a-(m-hydroxyphenyl)-cis-decahydroisoquinoline, mp 50°–52°.

NMR (CDCl$_3$): 7.15 (s, 5H); 7.45-6.5 (m, 4H); 3.8-1.2 (m, 24H).

Mass Spec.: Calcd for C$_{25}$H$_{33}$NO: 363.2560; Found: 363.2531.

EXAMPLE 15

N-(2-Furylethyl)-4a-(m-methoxyphenyl)-cis-decahydroisoquinoline

A.

N-(2-Furylethyl)-4a-(m-methoxyphenyl)-1,3-diketo-cis-decahydroisoquinoline

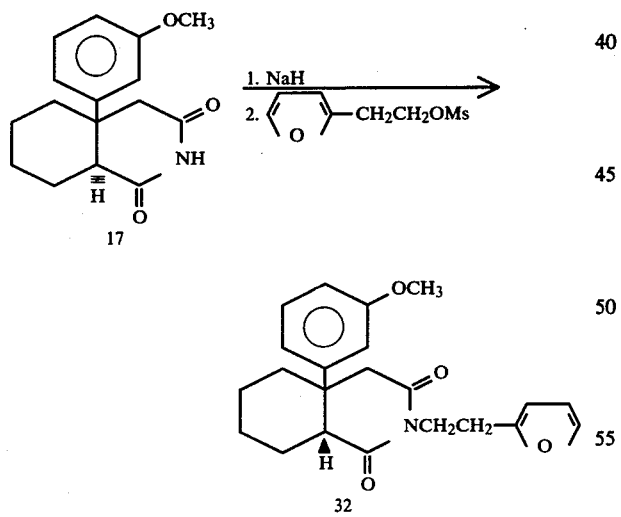

A solution of 5.0 g (18.5 mmoles) of 4a-(m-methoxyphenyl)-1,3-diketo-trans-decahydroisoquinoline in 100 ml of anhydrous dimethylformamide was added to a stirred suspension of 1.4 g (28 mmoles) of 50% sodium hydride in mineral oil (washed with pentane) in 75 ml of anhydrous dimethylformamide heated at 50° under nitrogen. The mixture was heated at 90° for 2 hours, then cooled to 35°. A solution of 7.1 g (37 mmoles) of freshly prepared 2-furylethyl mesylate (prepared according ot the procedure of Crossland and Servis, J. Org. Chem., 35, 3195 (1970)) in 10 ml of anhydrous dimethylformamide was added and the reaction mixture heated at 90° overnight. It was the cooled and poured into ice-water, and extracted with ether. Evaporation of the ether gave an oil which was purified by column chromatography (Silicar CC-7, eluting with acetone-benzene). The major fraction was identified as N-(2-furylethyl)-4a-(m-methoxyphenyl)-1,3-diketo-cis-decahydroisoquinoline.

NMR (CDCl$_3$): 7.4-7.1 (m, 2H); 7.0-6.6 (m, 3H); 6.2 (m, 1H); 5.9 (m, 1H); 4.2-3.3 (m, 1H); 3.77 (s, 3H); 3.2-2.2 (m, 7H); 2.0-1.1 (m, 7H).

B.

N-(2-Furylethyl)-4a-(m-methoxyphenyl)-cis-decahydroisoquinoline

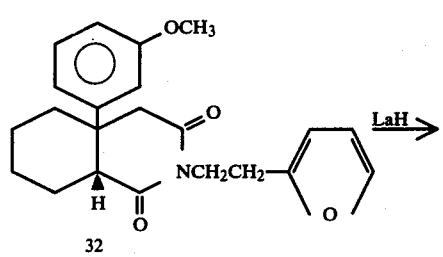

The product of Part A (6.3 g, 17.2 mmoles) in 250 ml of sodium-dried tetrahydrofuran was added to a stirred suspension of 6.3 g of lithium aluminum hydride in 100 ml of tetrahydrofuran under nitrogen, and the mixture was stirred at reflux for 20 hours. It was then cooled and treated successively with 6.3 ml of water, 6.3 ml of 3N sodium hydroxide and 18.9 ml of water. The inorganic salts were filtered and washed with ether. The combined filtrates were evaporated and the residual N-(2-furylethyl)-4a-(m-methoxyphenyl)-cis-decahydroisoquinoline was evaporatively distilled, bp 70° (0.0005 mm).

NMR (CDCl$_3$): 7.2 (m, 1H); 7.1-6.9 (m, 3H); 6.8-6.55 (m, 1H); 6.2 (m, 1H); 5.95 (m, 1H); 3.77 (s, 3H); 2.8-2.3 (m, 9H); 2.0-1.3 (m, 10H).

EXAMPLE 16

N-(3,3-Dimethylallyl)-4a-(m-hydroxyphenyl)-cis-decahydroisoquinoline

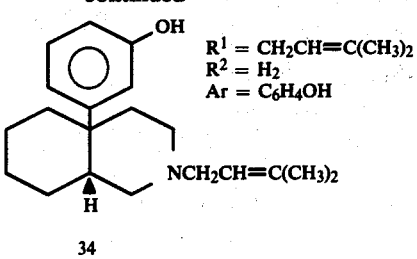

N-(3,3-Dimethylallyl)-4a-(m-methoxyphenyl)-cis-decahydroisoquinoline (1.2 g) and pyridine hydrochloride (5 g) were heated under nitrogen, for 1 hour at 200°. The reaction was worked up as in Example 8-B to give 400 mg, bp 240° (0.2 micron), of N-(3,3-dimethylallyl)-4a-(m-hydroxyphenyl)-cis-decahydroisoquinoline. Mass Spec.: Calcd for $C_{20}H_{29}NO$: 299.2248; Found: 299.2273.

EXAMPLE 17

N-methyl-4a-(p-fluorophenyl)-cis-decahydroisoquinoline

A. 2-(p-fluorophenyl)-cyclohexanone

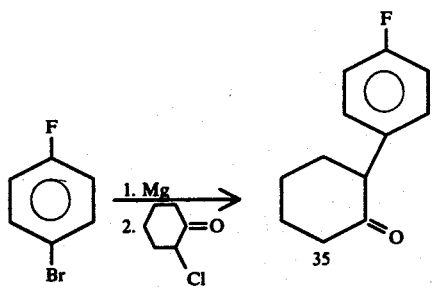

The Grignard reagent prepared by adding 210 g of p-fluorobromobenzene in 800 ml. of anhydrous ether to 29.1 g of magnesium turnings in 50 ml. of ether was added, with cooling to keep the temperature of the reaction less than 15° C., to a solution of 158.4 g of 2-chlorocyclohexanone in 800 ml. of anhydrous benzene. The reaction was stirred at 25° for 18 hrs. then the ether was distilled off and the resulting benzene solution refluxed for 24 hrs. It was then poured into a mixture of 1 liter water and 200 ml. hydrochloric acid and extracted with ether. After evaporation of the ether the residue was distilled to yield 117 g (51%), b.p. 115 (0.2 mm). The material solidified on standing and was recrystallized from hexane, m.p. 56°–59° C.

Anal. Calcd. for $C_{12}H_{13}FO$: C, 74.98; H, 6.82; Found: C, 74.24; H, 6.83.

B. 2-(p-fluorophenyl)-2-carbethoxymethylcyclohexanone

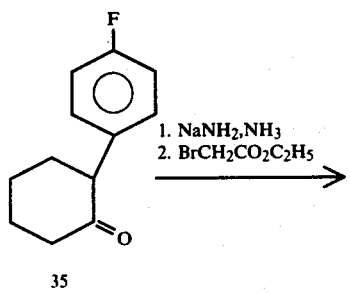

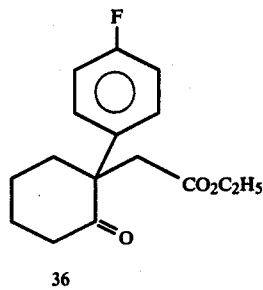

The product of Part A (117 g) in 120 ml. of anhydrous tetrahydrofuran was added to sodium amide (from 14.7 g sodium) in 2000 ml. of liquid ammonia. The reaction was stirred for 90 minutes then 68 ml α-bromoethyl acetate was added over 45 min. The reaction was stirred for 3 hrs. then the ammonia was allowed to slowly evaporate. Methanol (100 ml.) and water (1000 ml.) were added to the residue. Extraction with ether yielded the product, which when distilled, gave 115.4 g (68%), b.p. 134 (0.25 mm).

Anal. Calcd. for $C_{16}H_{19}FO_3$: C, 69.05; H, 6.88; Found: C, 68.97; H, 6.95.

C. 2-Cyano-3-(p-fluorophenyl)-3-carbethoxymethylcyclohexanone

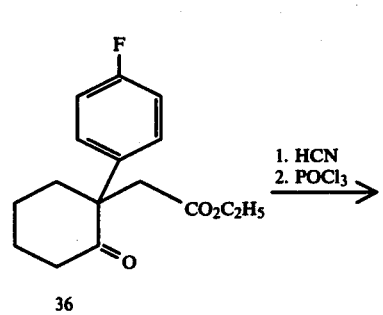

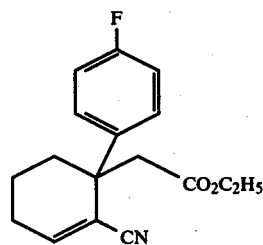

The product from Part B (50 g) was reacted in the manner described in Example 1, Part A, with 200 g of hydrogen cyanide and 12 drops of saturated aqueous potassium cyanide. Reaction of the product of this reaction with phosphorous oxychloride in pyridine (as described in Example 1, Part A) gave 2-cyano-3-(p-fluorophenyl)-3-carbethoxycyclohexene. Yield 33 g, b.p. 160° (0.35 mm).

D.
4a-(p-fluorophenyl)-1,3-diketo-1,2,3,4,4a,5,6,7-Octahydroisoquinoline

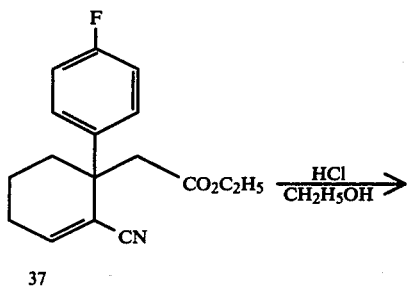

37

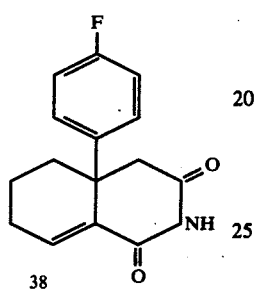

38

The product from Part C (75 g) was added to 500 ml. of anhydrous ethanol saturated with anhydrous hydrogen chloride and the mixture refluxed for 48 hrs. The solution was then concentrated, cooled, and the white precipitate collected.

Yield 32 g, m.p. 201–203. Anal. Calcd. for $C_{15}H_{14}FNO_2$: C, 69.49; H, 5.44; N, 5.40; Found: C, 69.30; H, 5.27; N, 5.02.

E.
N-methyl-4a-(p-fluorophenyl)-1,3-diketo-1,2,3,4,4a,5,6,7,-Octahydroisoquinoline

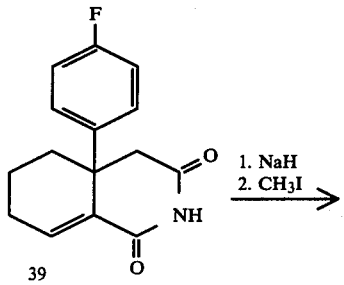

39

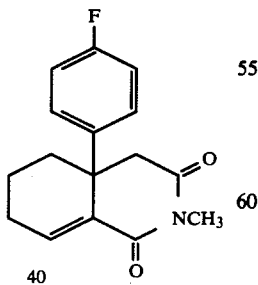

40

The product of part D (20 g) in 150 ml of anhydrous dimethylformamide was added to 3.35 g of a 55% suspension of sodium hydride in mineral oil in 100 ml. of dimethylformamide in the manner described in Example 1, Part C. Alkylation with 11.5 g of methyl iodide and workup (described in Example 1, Part C) gave N-methyl-4a-(p-fluorophenyl)-1,3,-diketo-1,2,3,4,4a,5,6,7,-octahydroisoquinoline, 12 g, m.p. 124–128.

F.
N-methyl-4a-(p-fluorophenyl)-1,3-diketo-trans-decahydroisoquinoline

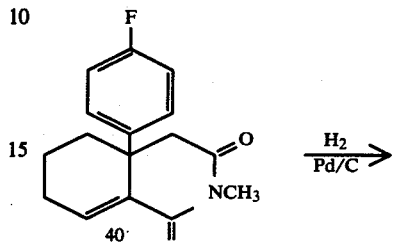

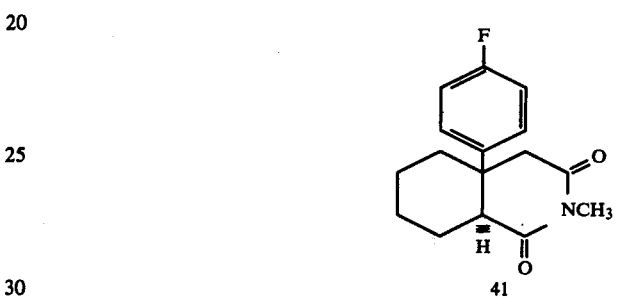

41

The product from Part E (12 g) in 150 ml. of ethanol and 50 ml. of glacial acetic acid was hydrogenated over 3 g of 5% palladium on carbon over 40 psi of hydrogen in the manner described in Example 1, Part D to give, after column chromatography on 350 g of silicon CC-7 and elution with benzene, 9 g, m.p. 141–143.

Anal. Calcd. for $C_{16}H_{18}F\ NO_2$: C, 69.80; H, 6.59; N, 5.09; Found: C, 69.81; H, 6.54; N, 5.08.

G.
N-methyl-4a-(p-fluorophenyl)-1,3,-diketo-cis-decahydroisoquinoline

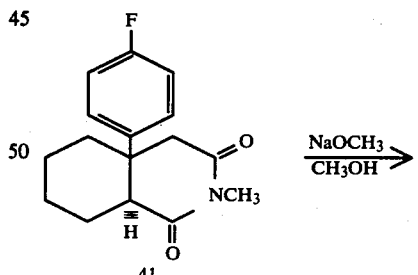

41

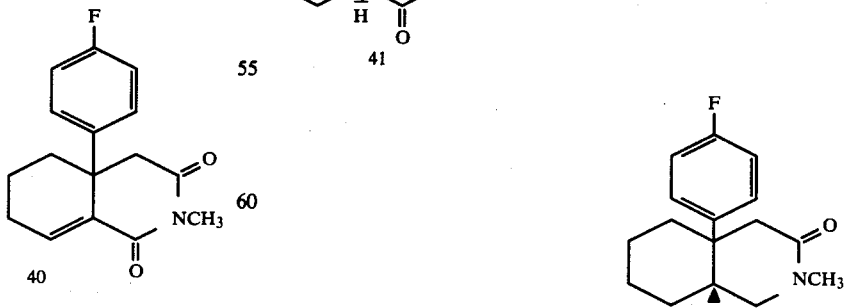

42

The product from Part F (2 g), 100 ml. of methanol and 400 mg of sodium methoxide was stirred at 25° for 4.8 hrs. after initially heating to reflux. The mixture was then poured into dilute hydrochloric acid and extracted with ether to yield a clear oil, 2 g.

NMR (CDCl₃) methylenes appear as broad singlet centered at 100 cps (8H); singlet at 181 cps (N—CH₃, 3H); multiplet plus quartet at 177,183,186,190 cps (CH₂CO and CHCO, 3H); multiplet at 410 to 450 cps (ArH,4H).

H. N-methyl-4a-(p-fluorophenyl)-cis-decahydroisoquinoline

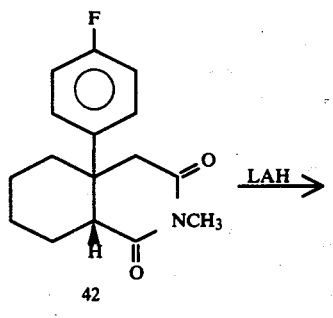

The product from Part G (2 g), 75 ml. of anhydrous tetrahydrofuran, and 2 g of lithium aluminum hydride were refluxed for 24 hrs. The reaction was worked up as described in Example 1, Part F to give 1.35 g, b.p. 110° (0.15 mm).

Anal. Calcd. for C₁₆H₂₂FN: C, 77.69; H, 8.97; N, 5.66; Found: C, 77.55; H, 9.10; N, 5.63.

By the above general procedure of Example 17 N-phenethyl-4a-(m-fluorophenyl)-cis-decahydroisoquinoline can be obtained.

EXAMPLE 18

Salts of N-phenethyl-4a-m-methoxyphenyl-cis-decahydroisoquinoline

When N-phenethyl-4a-m-methoxyphenyl-cis-decahydroisoquinoline is added to 0.1 to 3 N hydrochloric acid a white solid is obtained which can be recrystallized from ethanol. This hydrochloride has m.p. 220°-222° C. (decomp).

When N-phenethyl-4a-m-methoxyphenyl-cis-decahydroisoquinoline is mixed with a slight molar excess of maleic acid in hot acetonitrile it forms the crystalline maleate salt on cooling, m.p. 167°-168° C.

EXAMPLE 19

Dextro-N-methyl-4a-phenyl-cis-decahydroisoquinoline

A. laevo- and dextro-2-carboxymethyl-2-phenylcyclohexanone a-phenethylamine salt

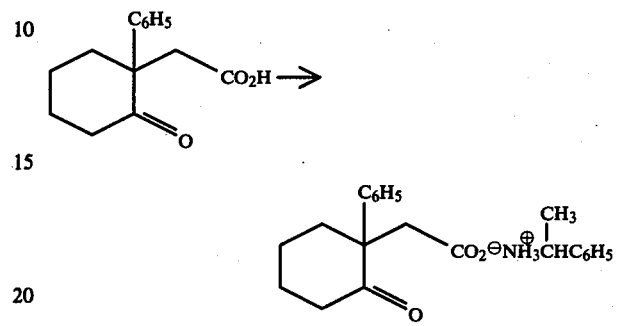

1. 2-Carboxymethyl-2-phenylcyclohexanone (Boekelheide et al., above) (40 g, 0.154 mole) obtained by alkaline hydrolysis of 2-carbethoxymethyl-2-phenylcyclohexanone was dissolved in 140 ml of hot ethanol and treated with 27 g of (+)-α-phenethylamine. The mixture was allowed to slowly crystallize to yield 21.8 g of the l-salt, m.p. 130°-132°, [α]$_D$—94. A second recrystallization from ethanol yielded material with m.p. 137°-139°, [α]$_D^{25°}$—142°. Further recrystallizations did not change the optical rotation.

2. The mother liquors from above were taken up in 6 N hydrochloric acid and the free acid extracted with ether. This material was dissolved in ethanol, treated with (—)-α-phenethylamine, and allowed to slowly crystallize. The white crystalline d-salt had m.p. 136°-137.5°, [α]$_D^{25°}$+141°.

B. laevo- and dextro-2-carboxymethyl-2-phenylcyclohexanone

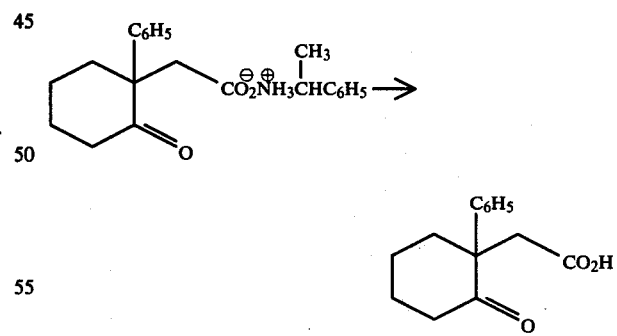

1. A solution of the product of Part A-1 (14.0 g) in 250 ml of cold 6 N hydrochloric acid was extracted with ether and treated as above to yield 9.6 g of the l-ketoacid m.p. 94°-95° [α]$_D^{25°}$—194 (c 1.04, CHCl₃).

2. A solution of the product of Part A-2 (15.9 g) in 250 ml of cold 6 N hydrochloric acid was extracted with ether. The ether extracts were dried with anhydrous magnesium sulfate, filtered and the ether evaporated to yield 10.0 g, of the d-ketoacid m.p. 94°-95°, [α]$_D^{25°}$+193° (c 1.03, CHCl₃).

C. laevo- and dextro-2-Carbethoxymethyl-2-phenylcyclohexanone

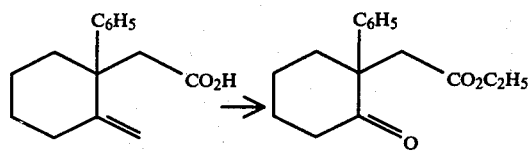

1. A solution of the product of Part B-1 (28 g) in 700 ml of ethanol containing 3 ml of concentrated sulfuric acid was refluxed in a soxhlet extractor apparatus with the thimble filled with 3 A molecular sieves. After refluxing for 24 hrs, excess potassium carbonate was added. The mixture was filtered and the solution evaporated. The residue was distilled to yield l-ketoester; a clear oil, b.p. 125° (0.1 mm), $[\alpha]_D^{25°} -207°$ (c 1.5, CHCl$_3$).

2. A solution of the product of Part B-2 (40 g) in 1000 ml of ethanol containing 8 ml of concentrated sulfuric acid was treated as above to yield, after distillation, the d-ketoester as a clear oil, b.p. 125° (0.1 mm), $[\alpha]_D^{25°} +234°$ (c 1.00, CHCl$_3$).

D. laevo- and dextro-2-cyano-3-phenyl-3-carbethoxymethylcyclohexene

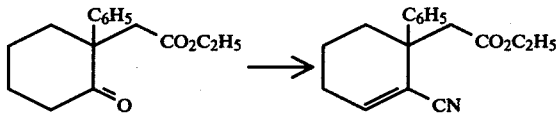

1. The product of Part C-1 (36 g, 0.138 mole), 200 ml of hydrogen cyanide and 12 drops of a saturated aqueous solution of potassium cyanide was stirred at 0° overnight. Concentrated sulfuric acid was added and the excess hydrogen cyanide evaporated. The residue was taken up in ether, washed successively with 0.1 N sulfuric acid, and brine, dried (Na$_2$SO$_4$), and evaporated. The residual oil was dissolved in 250 ml of pyridine and 50 ml of phosphorous oxychloride was added. The reaction mixture was stirred, under nitrogen, at reflux for 5 hours, then allowed to stand at 25° overnight. It was then poured into a mixture of 1 liter of ice-water and 200 ml of concentrated hydrochloric acid, and the resulting mixture was extracted with ether. The ether extract was washed with dilute hydrochloric acid, water and brine, then dried (Na$_2$SO$_4$) and evaporated. The residual oil was distilled yielding 28 g of the l-cyanoester, b.p. 130° (0.1 mm).

2. The product of Part C-2 (35 g, 0.134 mole) was treated as above to obtain 25 g of the d-cyanoester, b.p. 130° (0.1 mm).

E. dextro- and laevo-4a-Phenyl-1,3-diketo-1,2,3,4,4a,5,6,7-octahydroisoquinoline

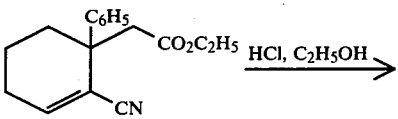

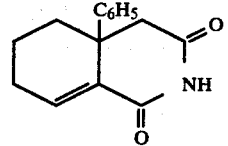

1. The product of Part D-1 (28 g), dissolved in 50 ml of absolute ethanol, was added to 600 ml of absolute ethanol previously saturated with anhydrous hydrogen chloride. The solution was refluxed under nitrogen for 48 hours. It was then cooled and concentrated. A white crystalline solid precipitated which was filtered, then recrystallized from ethanol to yield 12.0 g of the unsaturated d-imide, $[\alpha]_D^{25°} +219$ (c 1.00, CHCl$_3$).

2. The product of Part D-2 (17 g) in 40 ml of absolute ethanol was added to 400 ml of absolute ethanol previously saturated with anhydrous hydrogen chloride, then treated as above to yield 8.9 g of the unsaturated l-imide, m.p. 169-170, $[\alpha]_D^{25°} -208$ (c 1.20, CHCl$_3$).

In this example the sign of rotation changes in the ring-closing reactions.

F. dextro- and laevo-N-methyl-4a-phenyl-1,3-diketo-1,2,3,4,4a,5,6,7-octahydroisoquinoline

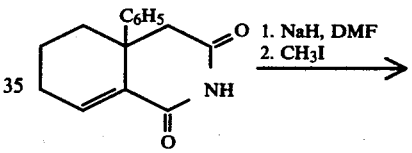

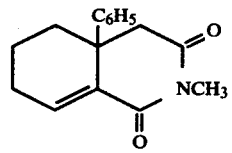

1. The product of Part E-1 (7.2 g, 29.9 mmoles) in 50 ml of dry dimethylformamide was added to 1.58 g of a 55.5% suspension of sodium hydride in mineral oil (36.5 mmoles NaH) in 50 ml of dimethylformamide, while the reaction mixture was maintained at 70° under nitrogen. The mixture was stirred and heated at 70° for 1 hour after the addition was completed, then cooled, and methyl iodide (8.5 g) in 20 ml of dimethylformamide was added dropwise. The mixture was heated at 90° for 30 min. then allowed to stand overnight at 25°. It was poured into water and extracted with ether. The ether extracts were dried (Na$_2$SO$_4$) and evaporated and the residue recrystallized from ethanol to yield 6.17 g of the unsaturated d-N-methylimide, m.p. 156°-158°, $[\alpha]_D^{25°} +245°$ (c 1.25, CHCl$_3$).

2. The product of Part E-2 (8.94 g, 37.1 mmole) in 60 ml of dimethylformamide was added to 1.96 g of a 55.5% suspension of sodium hydride in mineral oil in 50 ml of dimethylformamide as above to yield, after recrystallization in ethanol, 6.0 g of the unsaturated l-N-methylimide, m.p. 149°-153°, $[\alpha]_D^{25°} -258°$.

G. dextro- and laevo-N-methyl-4a-phenyl-1,3-diketo-trans decahydroisoquinoline

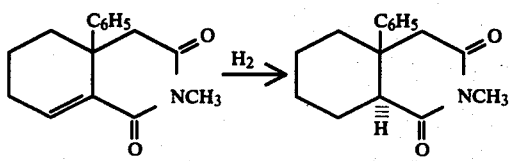

1. A mixture of the product of Part F-1 (6.1 g, 23.9 mmole), 100 ml of glacial acetic acid and 2 g of 5% palladium on carbon was shaken under 40 psi of hydrogen for 24 hours. The catalyst was removed by filtration and the solvent evaporated. Recrystallization of the residue from ethanol gave 3.7 g of the trans saturated d-N-methylimide, m.p. 189°–191°, $[\alpha]_D^{25} +81°$.

2. The product of Part F-2 (6.0 g, 23.5 mmoles) was treated as above to obtain 4.0 g of the trans saturated 1-N-methylimide, m.p. 159°–160°, $[\alpha]_D^{25} -72°$ (c, 1.02, CHCl$_3$).

H. Dextro-N-methyl-4a-phenyl-1,3-diketo-cis-decahydroisoquinoline

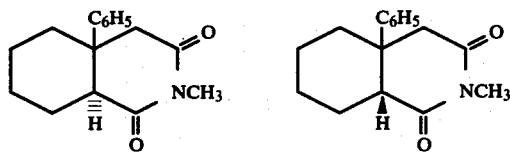

A mixture of 2 g of the product of G-1 above, 100 ml of methanol and 500 mg of sodium methoxide were refluxed for one hour then allowed to stand at 25° for 18 hrs. The reaction was worked up as described in Example 1, Part E to give an oil which was used without further purification.

I. d-N-methyl-4a-phenyl-cis-decahydroisoquinoline

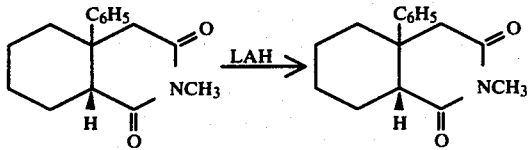

The crude product from Part H (2 g), 100 ml of anhydrous tetrahydrofuran and 2 g of lithium aluminum hydride were refluxed under nitrogen for 24 hrs. The reaction was quenched by the successive addition of 2 ml. of water, 2 ml. of 15% sodium hydroxide and 6 ml of water. The inorganic salts were filtered and the filtrate concentrated. The residue was evaporatively distilled to give a clear oil, b.p. 100° (0.07 mm), $[\alpha]_{365}^{25} +368°$. The picrate derivative was readily formed, m.p. 144°–147°.

EXAMPLE 20
N-(p-Tolylethyl)-4a-m-hydroxyphenyl-6β-methyl-cis-decahydroisoquinoline

A. 2-Methoxyphenyl-4-methylcyclohexanone

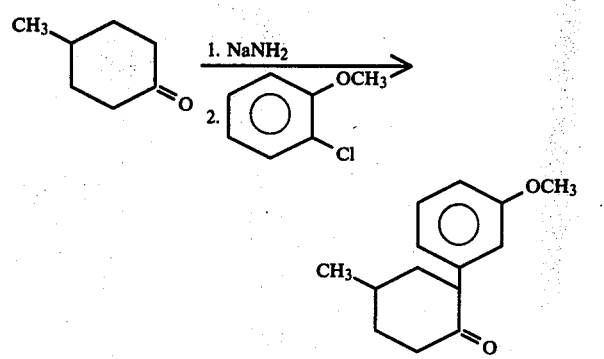

4-Methylcyclohexanone (224 g, 2 moles) was added dropwise rapidly to a cooled, stirred suspension of 170 g (4 moles) of sodium amide in 2 l of tetrahydrofuran under nitrogen. After the addition was complete, the ice bath was removed and the mixture was heated at reflux until the evolution of ammonia ceased (~3 hours). While still at reflux, 142.5 g (1 mole) of o-chloroanisole was added rapidly dropwise and the mixture was heated for an additional hour, until evolution of ammonia ceased.

The red-brown reaction mixture was cooled in an ice bath and excess sodium amide was quenched by the dropwise addition of a saturated aqueous solution of ammonium chloride. The mixture was poured into 3 l ice water, extracted with ether and the combined extracts washed with 3 N HCl and saturated sodium chloride, then dried (Na$_2$SO$_4$) and evaporated. The crude product was distilled under vacuum, bp 120°–130° at 0.15 mm Hg.

NMR (CDCl$_3$): δ 7.2 (quartet, J=8, 1H), 6.9–6.6 multiplet (3H), 3.78 (singlet, 3H), 2.7–1.5 (broad envelope, 8H), 1.1 (overlapping doublets, J=5.5, 3H).

B. 2-m-Methoxyphenyl-2-carbethoxymethyl-4-methylcyclohexanone

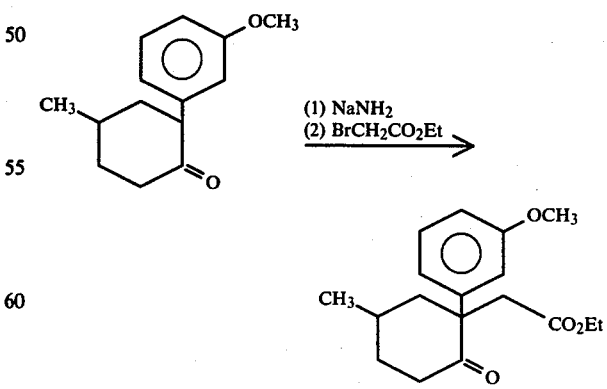

A solution of 142 g (0.65 mole) of the product from part A in 200 ml ether and 130 ml benzene was added rapidly dropwise to a suspension of 39 g (0.71 mole) of sodium amide in 330 ml ether stirred under nitrogen at room temperature. After the addition was complete, the mixture was heated at reflux for 4 hours, then cooled to −30° to −40° C. in a Dry Ice/acetone bath. Ethylbromoacetate (115 g, 0.60 mole) was added dropwise using an addition funnel without a sidearm, keeping the temperature below −30° C. during the addition. After stirring for one hour at −30° C. the reaction was allowed to warm to room temperature and was stirred overnight, poured into ice water, extracted with ether and dried the extracts (MgSO₄). The solvent was evaporated and the crude product distilled under vacuum, bp 130°–145° at 10 microns.

NMR (CDCl₃): δ 7.3-6.6 (multiplet, 4H), 4.2-3.8 (multiplet, 2H), 3.75 (singlet, 3H), 3.1-4.1 (broad envelope, 9H), 1.3-0.8 (multiplet, 6H).

IR: 3.4, 5.8, 6.2, 6.3, 6.7, 6.9, 7.0, 7.8, 7.9, 8.1, 8.4, 8.7, 9.6, 11.7, 12.8, 14.3μ.

C.
2-Cyano-3-m-methoxyphenyl-3-carbethoxymethyl-5-methylcyclohexene

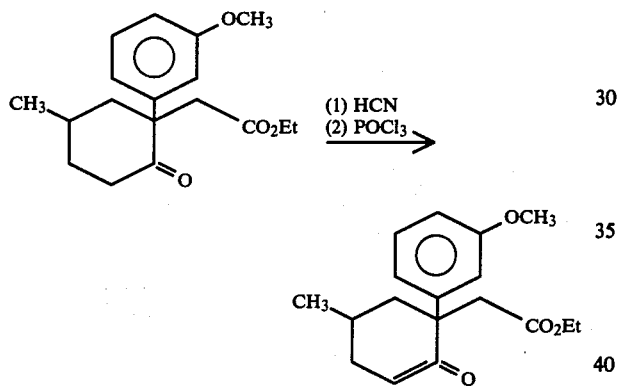

The product from part B (135 g) 300 ml of liquid hydrogen cyanide and 20 drops saturated aqueous potassium cyanide were stirred under nitrogen and packed in an ice bath for 20 hours. Concentrated sulfuric acid (20 drops) was added and the excess HCN evaporated. The crude cyanohydrin was taken up in ether, washed with 10% sulfuric acid, dried (MgSO₄) and evaporated. The residual oil was dissolved in 725 ml pyridine and 180 ml of phosphorous oxychloride was added. The solution was heated at reflux under nitrogen for 3 hours, cooled, poured into 4 l ice water containing 500 ml conc. hydrochloric acid and extracted with ether. The ether extracts were dried (Na₂SO₄) and evaporated. The product, a viscous oil, can be distilled by using a wiped-film Molecular Still (180° at 3 microns) or a short path still (bp 145°–155° at 3 microns).

NMR (CDCl₃): δ 7.4-6.7 (multiplet, 5H), 4.1 (quartet, J=7, 2H), 3.8 (singlet, 3H), 3.0 (multiplet, 2H), 3.2-2.5 (envelope, 7H), 1.25 (triplet, J=7, 3H), 0.9 (multiplet, 3H).

IR: 3.4, 4.5, 5.55, 6.2, 6.3, 6.7, 6.9, 7.0, 7.3, 7.7, 8.0, 8.2, 8.5, 9.6, 11.4, 12.8, 14.3μ.

D.
4a-m-Methoxyphenyl-6β-methyl-1,3-diketo-1,2,3,4,4a,5,6,7-octahydroisoquinoline

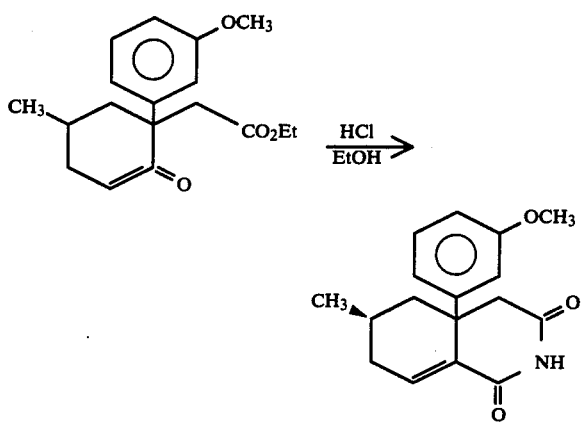

A solution of 112 g of the product from part C in 500 ml anhydrous ethanol was added to 2.5 l of anhydrous ethanol which had been saturated with anhydrous hydrogen chloride. The solution was heated at reflux under nitrogen for 3 days, then cooled to 0° in an ice bath. The fine white precipitate which had formed was filtered, washed with cold ethanol and dried. mp 214°–216°.

NMR (DMSO-d₆): δ 10.4 (singlet, 1H), 7.4-6.6 (multiplet, 5H), 3.65 (singlet, 3H), 3.7-3.5 (multiplet, 1H), 3.0 (broad singlet, 2H), 2.3-1.2 (envelope, 5H), 0.8 (doublet, J=4.5, 3H)

Anal. Calcd for C₁₇H₁₉NO₃: C, 71.56; H, 6.71; N, 4.91; Found: C, 71.90; H, 6.92; N, 4.94.

E.
4a-m-Methoxyphenyl-6β-methyl-1,3-diketo-trans-decahydroisoquinoline

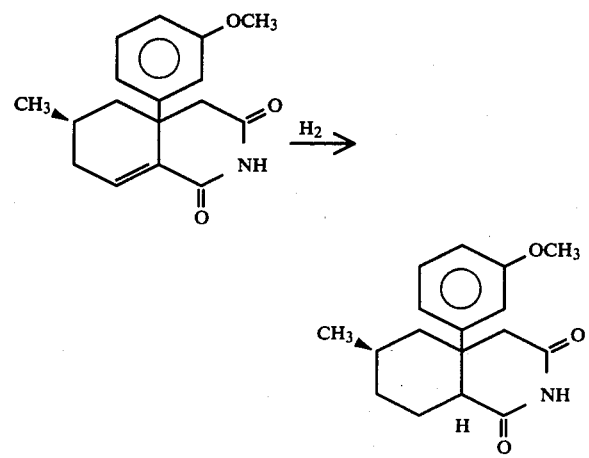

A mixture of the product from part D (10.5 g), 400 ml glacial acetic acid, 200 ml dioane and 2.0 g 5% palladium on activated carbon was shaken under 1000 psi of hydrogen at 40° C. for 6 hours. The catalyst was removed by filtration and the solvent evaporated from the filtrate. Recrystallization of the residue from ethanol yielded the product, mp 201°–202° C.

NMR (DMSO-d₆): δ 10.6 (singlet, 1H), 7.4-6.7 (multiplet, 4H), 3.72 (singlet, 3H), 3.0-26 (multiplet, 1H), 2.8

(singlet, 2H), 2.3-1.3 (envelope, 7H), 0.3 (doublet, J=7, 3H).

Anal. Calcd. for $C_{17}H_{21}NO_3$: C, 71.06; H, 7.37; N, 4.87; Found: C, 71.34; H, 7.50; N, 4.97.

F. N-(p-Tolylethyl)-4a-m-methoxyphenyl-6β-methyl-1,3-diketo-cis-decahydioisoquinoline

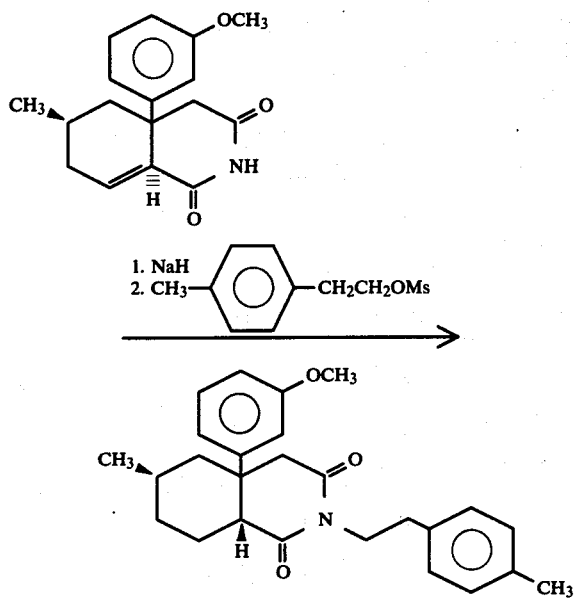

To a suspension of 5.6 g (117 mmole) of sodium hydride in 200 ml anhydrous dimethylformamide, stirred at 40° under $N_2$, was added 20 g (70 mmole) of the product from part E in 400 ml dry dimethylformamide. The mixture was heated to 90° until the evolution of hydrogen ceased (~2 hr), then cooled to 30°. A solution of 37.3 g (174 mmole) of the mesylate of 2-p-tolylethanol in 40 ml of anhy. dimethylformamide was added rapidly dropwise and the resultant solution was heated at 90° overnight. The reaction was cooled, poured into ice water and extracted with ether. The extract was dried ($Na_2SO_4$), evaporated, and on standing crystallized. The crystalline mass was filtered, washed with ether and dried. mp 108°-110°, single spot by TLC.

220 Hz NMR ($CDCl_3$): δ 7.43 (triplet, J=8, 1H), 7.25-6.9 (multiplet, 3H), 7.2 (doublet, J=6, 4H), 3.79 (triplet, J=8, 2H), 3.75 (singlet, 3H), 3.25-2.9 (AB, 2H), 3.1 (doublet of multiplets, 1H), 2.44 (triplet, J=8, 2H), 2.26 (singlet, 3H), 2.12 (multiplet, 1H), 1.95-1.55 (multiplet, 4H), 1.25-1.0 (multiplet, 2H), 0.9 (doublet, J=6).

G. N-(p-Tolylethyl)-4a-m-methoxyphenyl-6β-methyl-cis-decahydroisoquinoline

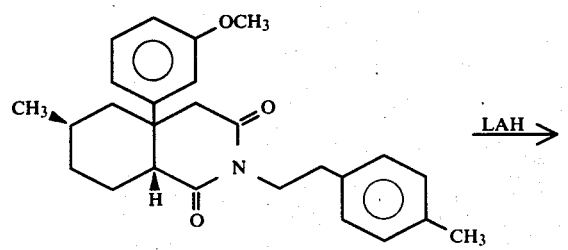

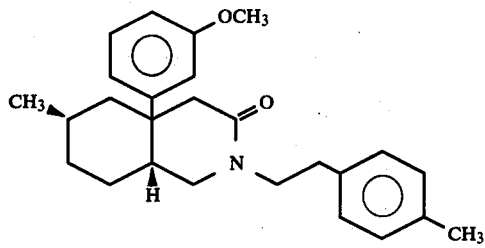

A solution of 21 g (0.05 mole) of the product from part F in 750 ml anhydrous tetrahydrofuran was added rapidly dropwise to a stirred suspension of 21 g (0.55 mole) of lithium aluminum hydride in 400 ml dry tetrahydrofuran, under nitrogen. The reaction mixture was heated at reflux overnight, then cooled and excess lithium aluminum hydride quenched by the dropwise addition of 21 ml water, 21 ml 3 N sodium hydroxide solution, and 63 ml water. The inorganic salts were filtered, washed with ether and the filtrate dried ($MgSO_4$) and evaporated.

The product oil can be evaporatively distilled at 150° at 3 microns; mp of hydrochloride salt 107°-109°.

NMR ($CDCl_3$): 7.4-6.9 (multiplet, 3H), 7.08 (singlet, 4H), 6.75 (multiplet, 1H), 3.8 (singlet, 3H), 2.9-1.0 (methylene envelope, 18H), 2.3 (singlet, 3H), 0.8 (doublet, J=6, 3H).

H. N-(p-Tolylethyl)-4a-m-hydroxyphenyl-6β-methyl-cis-decahydroisoquinoline

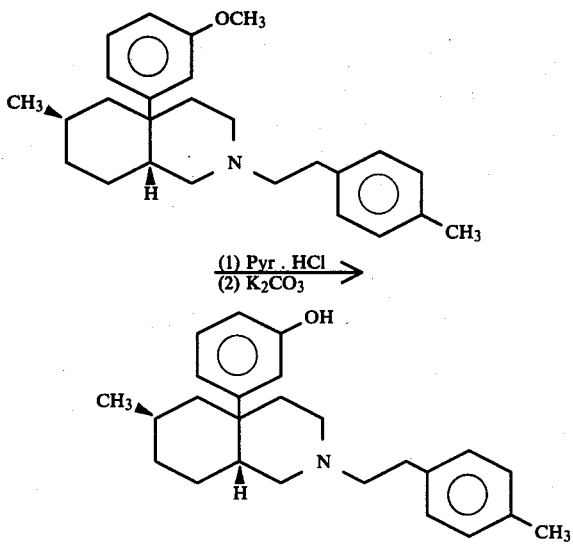

A mixture of 16.9 g (44.8 mmole) of the product from part G and 67 g (0.58 mole) of anydrous pyridine hydrochloride was heated at 195° under nitrogen for 3 hours. The mixture was cooled, dissolved in methylene chloride and washed with water, saturated potassium carbonate solution, and dried ($Na_2SO_4$). After removal of solvent the solid product was recrystallized from absolute ethanol. mp 150°-152°

Anal. Calcd. for $C_{25}H_{33}NO$: C, 82.60; H, 9.15; N, 3.85; Found: C, 82.16, 82.17; H, 9.24, 9.09; N, 3.86, 3.93.

NMR ($CDCl_3$): 7.3-6.5 (multiplet, 4H), 6.97 (singlet, 4H), 3.0-0.9 (methylene envelope of multiplets, 18H), 2.25 (singlet, 3H), 0.8 (doublet, J=6, 3H).

EXAMPLE 21

N-(p-Tolylethyl)-4a-m-hydroxyphenyl-6β-methyl cis-decahydroisoquinoline maleic acid salt

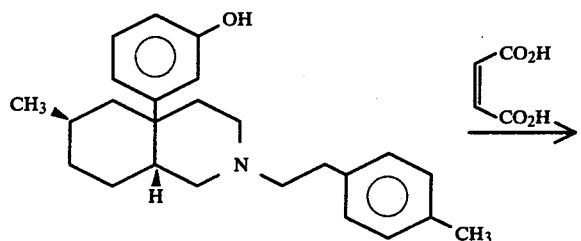

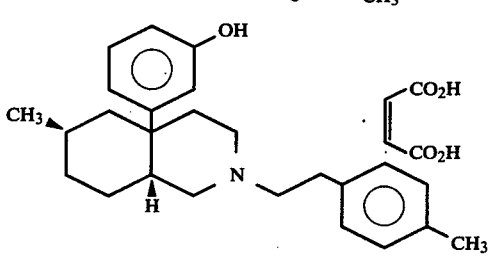

To a solution of 14 g (38.5 mmole) of the product from I-H in 70 ml of hot ethyl acetate was added 4.5 g (38.8 mmole) of maleic acid in 50 ml of hot ethyl acetate. The solution was cooled and the resultant crystalline salt was filtered and recrystallized from ethyl acetate; mp 168°-170°

Anal. Calcd. for $C_{29}H_{37}NO_5$: C, 72.62; H, 7.78; N, 2.92; Found: C, 72.83; H, 7.75; N, 3.06.

220 NMR (DMSO-d$_6$): δ 7.25 (triplet, J=8, 1H), 7.15 (singlet, 4H), 6.95-6.7 (multiplet, 3H), 6.1 (singlet, 2H), 3.5-1.5 (methylene envelope of many multiplets, 16H), 2.25 (singlet, 3H), 1.0 (multiplet, 2H), 0.8 (doublet, J=6, 3H).

EXAMPLE 22

N-Cyclobutylmethyl-4a-m-hydroxyphenyl-6β-methyl-cis-decahydroisoquinoline

A.

N-Cyclobutylmethyl-4a-m-methoxyphenyl-6β-methyl-1,3-diketo-cis-decahydroisoquinoline

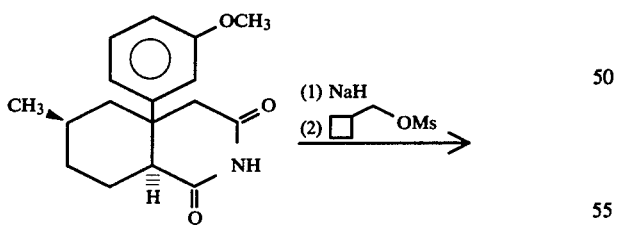

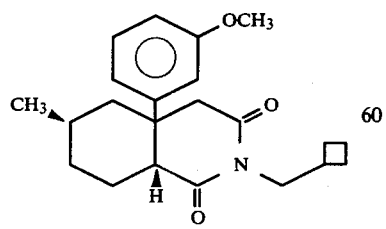

To a suspension of 0.7 g (14 mmole) of sodium hydride in 40 ml anhydrous dimethylformamide, stirred at 40° under nitrogen, was added rapidly dropwise a solution of 2.5 g (8.7 mmole) of 4a-m-methoxyphenyl-6β-methyl-1,3-diketo-trans-decahydroisoquinoline in 50 ml anhydrous dimethylformamide. The mixture was heated at 90° for 3 hours, cooled to room temperature, and 2.85 g (17.4 mmole) of the mesylate of cyclobutanemethanol in 5 ml anhydrous dimethylformamide was added. The mixture was heated at 90° overnight, cooled, poured into water and extracted with ether. The extract was washed with water, dried (Na$_2$SO$_4$) and evaporated. The crude product oil was column chromatographed on Florisil and eluted with 2% acetone-benzene.

NMR (CDCl$_3$): δ 7.4-7.0 (quartet, J=8, 1H), 7.0-6.6 (multiplet, 3H), 3.75 (singlet, 3H), 3.7-3.0 (multiplet, 5H), 2.4-1.1 (envelope, 14H), 0.9 (doublet, J=5, 3H).

IR: 3.4, 5.8, 6.0, 6.2, 6.3, 6.85, 6.9, 7.0, 7.2, 7.4, 7.5, 7.75, 7.9, 8.1, 8.3, 8.5, 8.7, 8.9, 9.5, 11.7, 12.8, 13.6, 14.3μ.

B.

N-Cyclobutylmethyl-4a-m-methoxyphenyl-6β-methyl-cis-decahydroisoquinoline

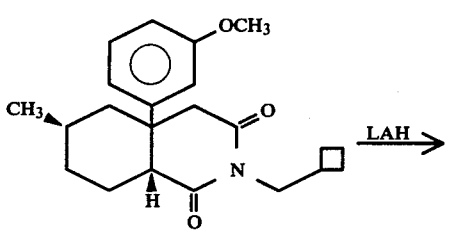

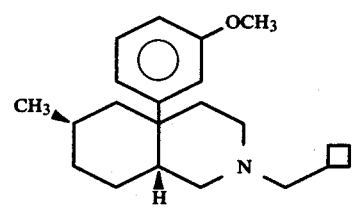

A solution of 2.3 g (6.47 mmole) of the product from part A in 100 ml of anhydrous tetrahydrofuran was added dropwise to a suspension of 2.3 g of lithium aluminum hydride in 65 ml dry tetrahydrofuran stirred under nitrogen. The suspension was heated at reflux overnight, cooled and excess reagent quenched by the dropwise addition of 2.3 ml water, 2.3 ml 3 N sodium hydroxide, 6.9 ml water. Filtration of the inorganic salts and evaporation of the filtrate yielded the product as a clear viscous oil.

NMR (CDCl$_3$): δ 7.4-6.6 (multiplet, 4H), 3.8 (singlet, 3H), 2.8-1.2 (envelope, 21H), 1.0 multiplet, 2H), 0.8 (doublet, J=6, 3H).

IR: 3.4, 6.2, 6.3, 6.7, 6.85, 6.9, 7.0, 7.8, 7.95, 8.1, 9.5, 12.9, 14.15, 14.4μ.

C.

N-Cyclobutylmethyl-4a-m-hydroxyphenyl-6β-methyl-cis-decahydroisoquinoline

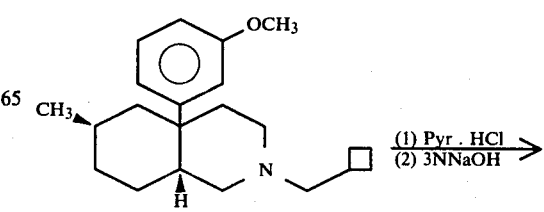

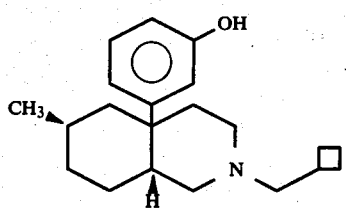

A mixture of 1.7 g (5.2 mmole) of the product from part B and 6.0 g (52 mmole) of anhydrous pyridine hydrochloride was heated under nitrogen at 190° for 3 hr, then cooled to room temperature. It was dissolved in chloroform, washed with water, dried (Na$_2$SO$_4$) and the solvent evaporated. The crude product was dissolved in tetrahydrofuran and stirred with 3 N sodium hydroxide solution for 3 hours. Ether was added and the ether-tetrahydrofuran layer was washed with water, dried (Na$_2$SO$_4$) and evaporated. The oil was stirred with ether until a solid precipitate formed which was filtered and recrystallized from absolute ethanol, mp 148°–150°.

Alternatively the product oil can be evaporatively distilled at 170°–180° at 3 microns and the resultant glass recrystallized from ethanol.

NMR (CDCl$_3$): δ 7.4-6.6 (multiplet, 4H), 2.8-1.2 (methylene envelope, 21H), 1.0 (multiplet, 2H), 0.8 (doublet, J=6, 3H).

EXAMPLE 23

N-Methyl-4a-m-methoxyphenyl-6β-methyl-cis-decahydroisoquinoline

A.

N-Methyl-4a-m-methoxyphenyl-6β-methyl-1,3-diketo-cis-decahydroisoquinoline

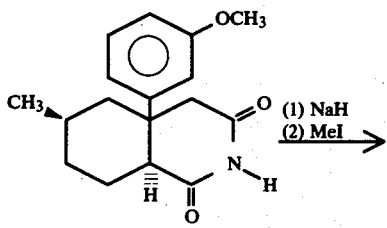

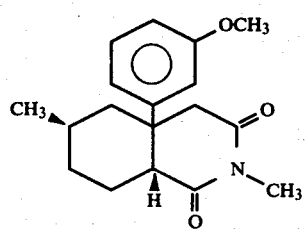

To a suspension of 5.6 g (116 mmole) of sodium hydride in 320 ml of anhydrous dimethylformamide, stirred at 40° under nitrogen, was added a solution of 20 g (69 mmole) of 4a-m-methoxyphenyl-6β-methyl-trans-decahydroisoquinoline in 400 ml dry dimethylformamide. The mixture was heated at 90° for 3 hours, cooled to room temperature, and 19.8 g (139 mmole) of methyl iodide in 40 ml dry dimethylformamide was added rapidly dropwise. The reaction mixture was heated at 90° overnight, cooled, poured into ice water and extracted with ether. The extract was washed with water, dried (Na$_2$SO$_4$) and evaporated. The crude product oil was column chromatographed on silica gel, eluting with benzene and 1% acetone-benzene. TLC shows single spot.

NMR (CDCl$_3$): δ 7.2 (quartet, J=8, 1 H), 7.0-6.6 (multiplet, 3H), 3.78 (singlet, 3H), 3.2-2.9 (multiplet, 3H), 2.97 (singlet, 3H), 2.2-1.0 (envelope, 7H), 0.9 (doublet, J=5, 3H).

IR: 3.35, 5.75, 5.95, 6.2, 6.3, 6.75, 6.8, 6.9, 7.65, 7.95, 8.6, 8.9, 9.5, 12.8, 14.3, 14.7μ.

B.

N-Methyl-4a-m-methoxyphenyl-6β-methyl-cis-decahydroisoquinoline

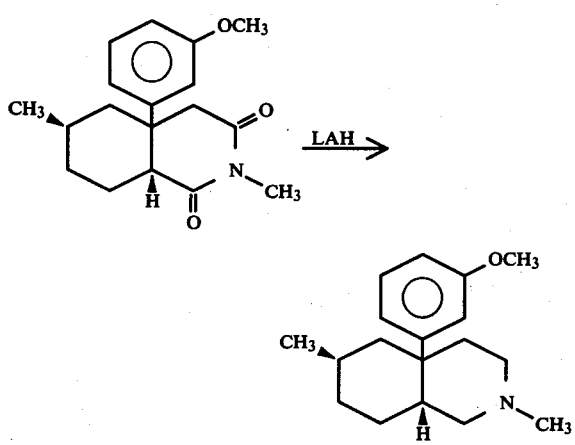

A solution of 11.3 g (37.5 mmole) of the product from part A in 400 ml anhydrous tetrahydrofuran was added dropwise to a suspension of 11.3 g (0.3 mole) of lithium aluminum hydride in 200 ml anhydrous tetrahydrofuran, stirred under nitrogen. The mixture was heated at reflux overnight, cooled, and excess reagent quenched by the dropwise addition of 11.3 ml water, 11.3 ml 3 N sodium hydroxide solution, and 33.9 ml water. The inorganic salts were filtered off and the filtrate evaporated yielding the product as a clear viscous oil; mp of picrate (recrystallized from benzene) 162°–164°

NMR (CDCl$_3$): δ 7.24 (quartet, J=8, 1H), 7.02 (multiplet, 2H), 6.9-6.65 (multiplet, 1H), 3.85 (singlet, 3H), 2.1 (singlet, 3H), 2.9-1.0 (envelope, 14H), 0.8 (doublet, J=6, 3H).

IR: 3.4, 6.2, 6.3, 6.75, 6.85, 6.9, 7.0, 7.8, 8.1, 9.5, 9.6, 12.9, 14.1, 14.4μ.

Mass Spec. Calc. for C$_{18}$H$_{27}$ON: 273.2091; Found: 273.2106.

EXAMPLE 24

4a-m-Methoxyphenyl-6β-methyl-cis-decahydroisoquinoline

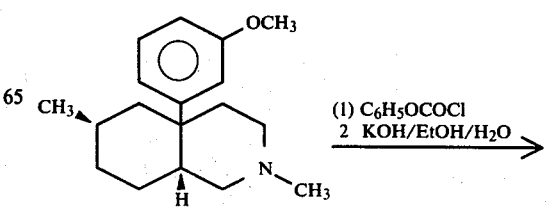

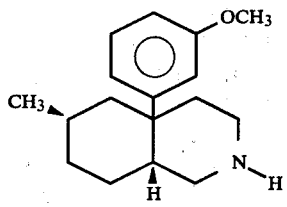

To a solution of 8.8 g (32.2 mmole) of N-methyl-4a-m-methoxyphenyl-6β-methyl-cis-decahydroisoquinoline in 70 ml of methylene chloride, stirred at room temperature under nitrogen, was added a solution of 6.3 g (40.2 mmole) of phenylchloroformate in 20 ml of methylene chloride. The resultant solution was heated at reflux for 2.5 hr, then stirred at room temperature overnight. The solvent was evaporated and the residual oil was heated at reflux in 100 ml of 5% sodium hydroxide solution under nitrogen for 30 minutes. After cooling the reaction was extracted with ether. The ether extracts were washed with 3 N hydrochloric acid to remove unreacted amine (1.5 g recovered), then dried and evaporated.

The phenylurethane product was dissolved in 240 ml absolute ethanol and 50 ml of 50% aqueous potassium hydroxide was added. The mixture was heated at reflux for 3 days under nitrogen, then cooled and ethanol removed under vacuum. The aqueous residue was extracted with ether and the ether extract was dried (Na$_2$SO$_4$) and evaporated. The resultant oil was dissolved in 250 ml of 3 N hydrochloric acid, washed with ether, made strongly basic with 50% aqueous sodium hydroxide and extracted with ether. The ether extract was dried (Na$_2$SO$_4$) and evaporated, yielding the product as a clear viscous oil.

NMR (CDCl$_3$): δ 7.2 (quartet, J=8, 1H), 7.1-6.9 (multiplet, 2H), 6.8-6.6 (multiplet, 1H), 3.8 (singlet, 3H), 3.1-0.9 (methylene envelope, 15H), 0.8 (doublet, J=6, 3H).

IR: 3.0, 3.4, 6.25, 6.35, 6.7, 6.9, 7.8, 8.0, 8.1, 9.5, 12.8, 14.3μ.

EXAMPLE 25

4-a-m-Methoxyphenyl-cis-decahydroisoquinoline

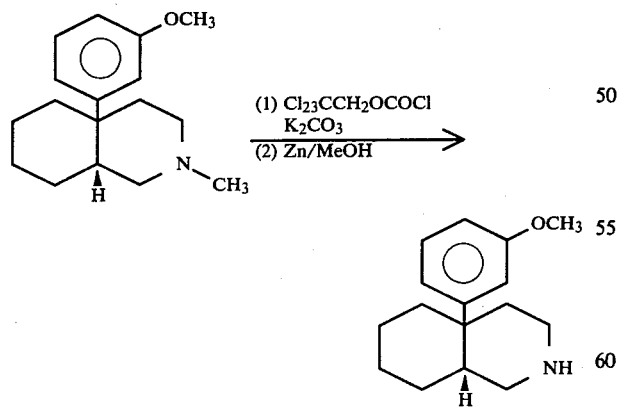

To a solution of 4.2 g (16.2 mmole) of N-methyl-4a-m-methoxyphenyl-cis-decahydroisoquinoline in 100 ml benzene, stirred at room temperature under nitrogen, was added 11.2 g (81.1 mmole) anhydrous potassium carbonate and 5.2 g (24.5 mmole) of trichloroethyl chloroformate in 80 ml benzene. The resultant suspension was heated at reflux for 48 hours, cooled and diluted with 200 ml of ether. The organic solution was washed with water and 3 N hydrochloric acid and dried (Na$_2$SO$_4$). Evaporation left an oil which was purified by column chromatography on silica gel eluting with benzene.

A sample of the urethane product obtained (3.7 g, 8.8 mmole) was dissolved in 150 ml of methanol and stirred at room temperature. Zinc powder (2.86 g, 44 mmole) was added and the suspension heated at reflux under nitrogen for 24 hours. The reaction was then cooled and the zinc filtered off. The filtrate was diluted with 3 N sodium hydroxide solution and extracted with ether. The ether extracts were dried (K$_2$CO$_3$) and solvent evaporated. The product oil was evaporatively distilled at 110° at 0.5 microns Hg.

NMR (CDCl$_3$): δ 7.4-6.6 (multiplet, 4H), 3.8 (singlet, 3H), 3.0-2.7 (multiplet, 2H), 2.6-1.2 (methylene envelope, 12H).

IR: 3.4, 6.25, 6.35, 6.7-7.0, 7.8, 8.1, 9.5, 13.0, 14.3μ.

EXAMPLE 26

N-(p-Tolyethyl)-4a-m-methoxyphenyl-6β-methyl-cis-decahydroisoquinoline (same prod. as Example 20-G)

A.

N-(p-Tolyacetyl)-4a-m-methoxyphenyl-6β-methyl-cis-decahydroisoquinoline

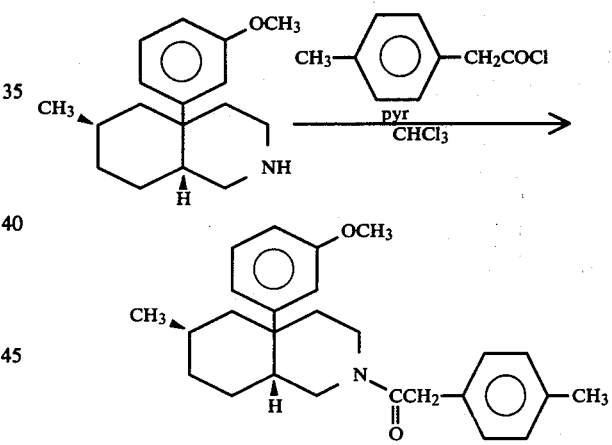

To a solution of 3.8 g (14.7 mmole) of 4-a-m-methoxyphenyl-6β-methyl-cis-decahydroisoquinoline in 120 ml of chloroform, stirred under N$_2$ at 0°, was added 1.4 ml (17.6 mmole) of pyridine and 3.0 g (17.6 mmole) of p-tolylacetic acid chloride in 5 ml chloroform. The solution was stirred at 0° for 2.5 hr and then at room temperature for 2.5 days. The chloroform solution was poured into 120 ml of 3 N hydrochloric acid, separated, washed with saturated sodium bicarbonate solution, dried (Na$_2$SO$_4$) and evaporated. The crude amide was column chromatographed on silica gel and eluted with 2-5% acetone-benzene.

NMR (CDCl$_3$): δ 7.5-6.6 (multiplet, 4H), 7.13 (doublet, J=2, 4H), 3.8 (singlet, 3H), 3.7 (doublet, J=2.5, 2H), 3.5-0.9 (methylene envelope of multiplets, 14H), 0.8 (doublet, J=5, 3H).

IR: 3.35, 6.05, 6.2, 6.3, 6.75, 6.9, 7.75, 7.95, 8.1, 9.0, 9.6, 12.9μ.

B.
N-(p-Tolylethyl)-4-a-m-methoxyphenyl-6β-methyl-cis decahydroisoquinoline

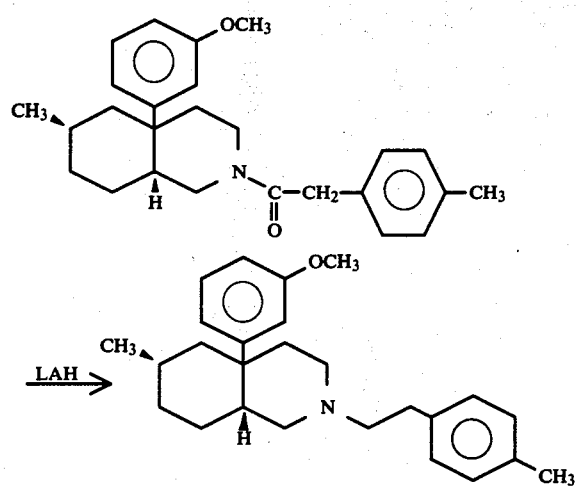

To a suspension of 1.0 g (26 mmole) of lithium aluminum hydride in 40 ml anhydrous tetrahydrofuran, stirred under nitrogen, was added 2.7 g (6.9 mmole) of the product from part A, and the suspension was heated at reflux overnight. It was then cooled and the excess lithium aluminum hydried quenched by the addition of 1 ml water, 1 ml 3 N sodium hydroxide solution and 3 ml water. The inorganic salts were removed by filtration and the filtrate was evaporated.

NMR is the same as product from Example 20 G.

EXAMPLE 27

N-Phenethyl-4a-m-hydroxyphenyl-6β-methyl-cis-decahydroisoquinoline

A.
N-Phenethyl-4a-m-methoxyphenyl-6β-methyl-1,3-diketo-cis-decahydroisoquinoline

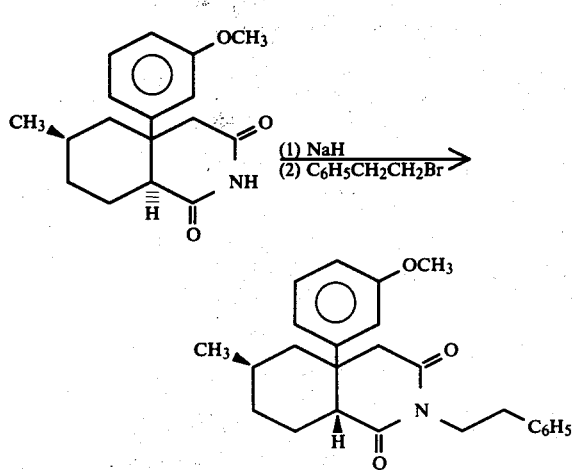

To a suspension of 2.25 g (47 mmole) of sodium hydride in 130 ml anhydrous dimethylformamide, stirred at 40° under $N_2$, was added 8.0 g (28 mmole) of 4a-m-methoxyphenyl-6β-methyl-1,3-diketo-trans-decahydroisoquinoline in 160 ml of anhydrous dimethylformamide. The mixture was heated to 90° until the evolution of hydrogen ceased (~2 hr), then cooled to 30°. A solution of 7.6 ml (55.7 mmole) of (2-bromoethyl)-benzene in 10 ml anhydrous dimethylformamide was added rapidly dropwise and the resultant solution was heated at 90° overnight. The reaction was cooled, poured into ice-water and extracted with ether. The extract was dried ($Na_2SO_4$), evaporated, and column chromatographed on Silicar CC-7 (silica gel) eluting with benzene and 2% acetone-benzene.

NMR (CDCl$_3$): δ 7.4-6.6 (multiplet, 9H), 3.8 (triplet, J=7, 2H), 3.7 (Singlet, 3H), 3.1-1.0 (multiplets, 12H), 0.88 (doublet, J=5, 3H).

B.
N-Phenethyl-4a-m-methoxyphenyl-6β-methyl-cis-decahydroisoquinoline

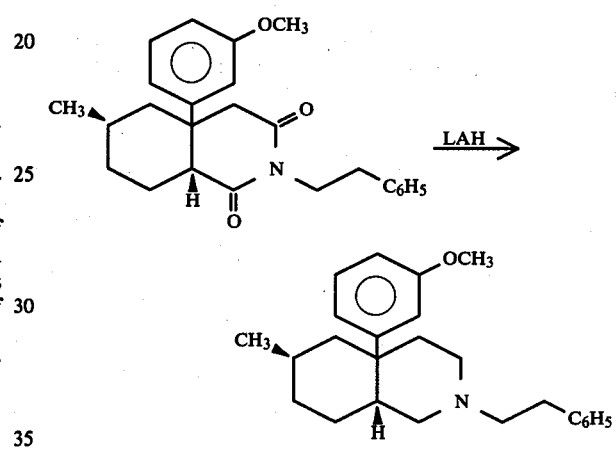

A solution of 7.0 g (17.9 mmole) of the product from part A in 300 ml anhydrous tetrahydrofuran was added rapidly dropwise to a stirred suspension of 7.0 g (183 mmole) of lithium aluminum hydride in 150 ml anhydrous tetrahydrofuran under nitrogen. The reaction mixture was heated at reflux overnight, then cooled and the excess lithium aluminum hydride quenched by adding successively 7 ml water, 7 ml 3 N sodium hydroxide, 21 ml water. The inorganic salts were filtered, washed with ether, and the filtrate dried (MgSO$_4$) and evaporated. The hydrochloride salt had mp of 118°-120°.

NMR (CDCl$_3$): δ 7.3-6.8 (multiplet, 3H), 7.1 (singlet, 5H), 6.8-6.6 (multiplet, 1H), 3.7 (singlet, 3H), 2.9-0.9 (multiplets, 18H), 0.8 (doublet, J=5, 3H).

IR: 3.4, 6.2, 6.3, 6.7, 6.8, 6.9, 7.0, 7.75, 7.9, 8.1, 9.1, 9.5, 12.9, 14.3μ

C.
N-Phenethyl-4a-m-hydroxyphenyl-6β-methyl-cis-decahydroisoquinoline

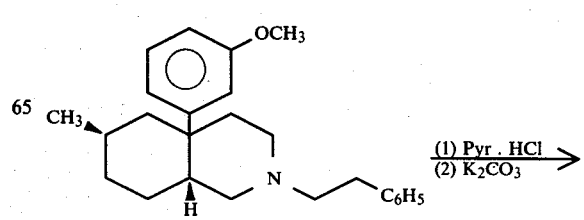

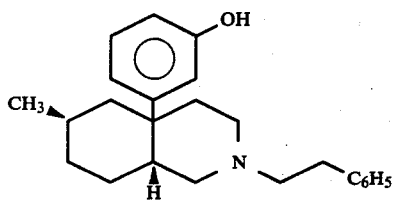

A mixture of 5.0 g (13.8 mmole) of the product from part B and 20 g (173 mmole) of anhydrous pyridine hydrochloride was heated at 195° under nitrogen for 3 hrs. The mixture was cooled, dissolved in methylene chloride and washed with water, saturated potassium carbonate and dried ($Na_2SO_4$). After removal of solvent, the product was recrystallized from ethanol, mp 174°-175°

Anal. Calcd. for $C_{24}H_{31}NO$: C, 82.48; H, 8.94; N, 4.01; Found: C, 82.11, 82.22; H, 8.91, 8.67; N, 4.10, 4.05.

NMR ($CDCl_3$) δ 7.4-6.6 (multiplet, 9H), 3.0-0.9 (multiplets, 18H), 0.8 (doublet, J=5, 3H).

EXAMPLE 28

N-(2-Furylmethyl)-4a-m-methoxyphenyl-6β-methyl-cis-decahydroisoquinoline

A.

N-(2-Furoyl)-4a-m-methoxyphenyl-6β-methyl-cis-decahydroisoquinoline

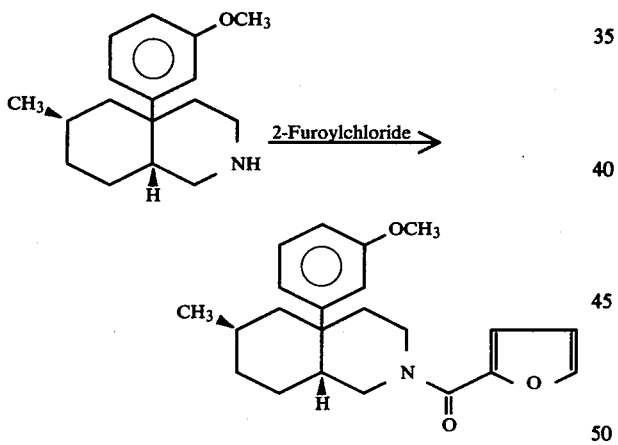

To a solution of 1.9 g (7.3 mmole) of 4a-m-methoxyphenyl-6β-methyl-cis-decahydroisoquinoline in 60 ml of chloroform, stirred under nitrogen at 0°, was added 0.75 ml (9.4 mmole) of pyridine and 0.9 ml (9.1 mmole) of 2-furoylchloride in 5 ml chloroform. The solution was stirred at 0° for 2 hr and then at room temperature overnight. The chloroform solution was poured into 60 ml of 3 N hydrochloric acid, separated, washed with saturated sodium bicarbonate, dried ($Na_2SO_4$) and evaporated. The crude amide was column chromatographed on silica gel eluting with benzene and ether-benzene mixtures.

NMR ($CDCl_3$): δ 7.6-6.4 (multiplets, 7H), 3.8 (singlet, 3H), 3.3-0.9 (multiplets 14H), 0.8 (doublet, J=6, 3H).

IR: 3.3, 5.7, 6.1, 6.3, 6.7, 6.9, 7.7, 7.9, 8.0, 8.4, 8.5, 9.0, 9.6, 9.85, 13.2μ

B.

N-(2-Furylmethyl)-4a-m-methoxyphenyl-6β-methyl-cis-decahydroisoquinoline

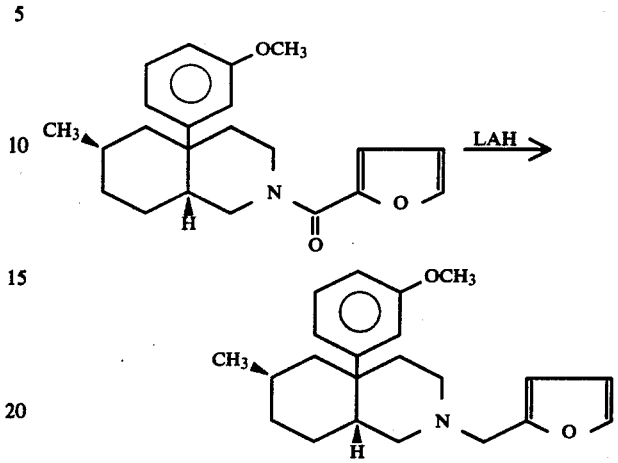

To a suspension of 0.5 g (13.1 mmole) of lithium aluminum hydride in 25 ml anhydrous tetrahydrofuran, stirred under nitrogen, was added 1.2 g (3.4 mmole) of the product from part A, and the suspension was heated at reflux overnight. It was then cooled and the excess lithium aluminum hydride quenched by the addition of 0.5 ml water, 0.5 ml of 3 N sodium hydroxide and 1.5 ml water. The inorganic salts were filtered and washed with ether and the filtrate evaporated. The viscous oil product can be evaporatively distilled at 125°-130° at 3 microns.

NMR ($CDCl_3$) δ 7.3-7.1 (multiplet, 2H), 7.0-6.85 (multiplet, 2H), 6.85-6.55 (multiplet, 1H), 6.3-6.0 (multiplet, 2H), 3.8 (singlet, 3H), 3.3 (multiplet, 2H), 2.8-0.9 (multiplet, 14H), 0.8 (doublet, J=6, 3H).

IR: 3.4, 6.2, 6.3, 6.7, 6.8, 6.9, 7.0, 7.5, 7.8, 7.95, 8.1, 8.7, 9.6, 9.9, 13.0, 13.7, 14.1, 14.4μ.

EXAMPLE 29

N-Cyclopropylmethyl-6-methyl-4a-(m-methoxyphenyl)-cis-decahydroisoquinoline

A.

N-cyclopropylmethyl-4a-(m-methoxyphenyl)-6-methyl-1,3-diketo-cis-decahydroisoquinoline

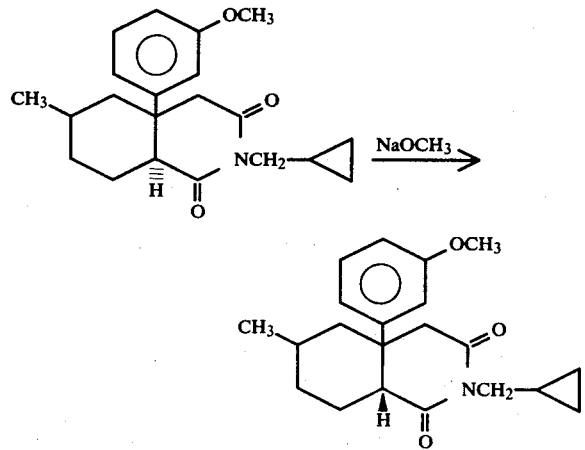

N-Cyclopropylmethyl-4a-(m-methoxyphenyl)-6-methyl-1,3-diketo-trans-decahydroisoquinoline (4.0 g, 11.7 mmoles), sodium methoxide (0.5 g) and 100 ml of methanol were heated to reflux for 18 hours. The mixture was cooled, concentrated on a rotary evaporator and diluted with water. The product was extracted with ether to yield, after evaporation of the ether, a viscous oil. This material was used in part B without further purification.

B.
N-cyclopropylmethyl-6-methyl-4a-(m-methoxyphenyl)-cis-decahydroisoquinoline

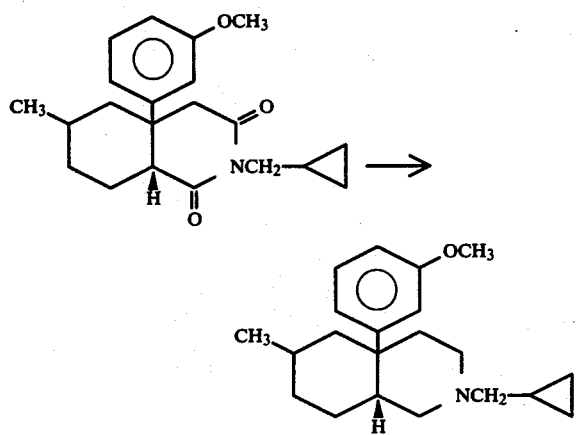

Product from Part A (3.0 g), tetrahydrofuran (75 ml) and lithium aluminum hydride (3 g) were refluxed for 18 hours. The mixture was cooled and 3 ml of water, 3 ml of 15% aqueous sodium hydroxide and 9 ml of water were added successively. The inorganic salts were filtered and the filtrate evaporated. The residual oil was evaporatively distilled to yield 2.8 g, bp 130° (1μ).

EXAMPLE 30
N-cyclopropylmethyl-6-methyl-4a-(m-hydroxyphenyl)-cis-decahydroisoquinoline

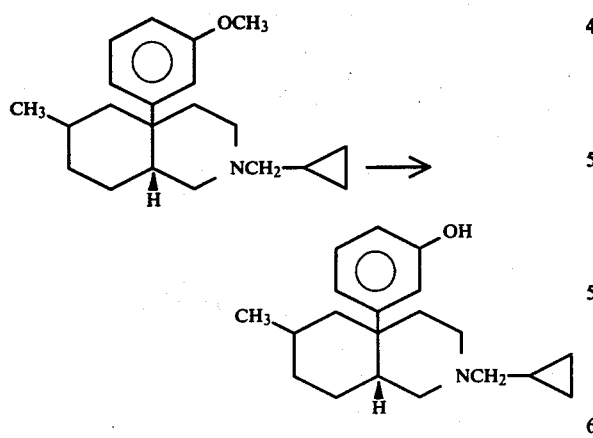

N-cyclopropylmethyl-6-methyl-4a-(m-methoxyphenyl)-cis-decahydroisoquinoline (2.8 g) and anhydrous pyridine hydrochloride (12 g) were heated at 190° for 1 hour. The mixture was cooled, diluted with water, basified with potassium carbonate and extracted with methylene chloride. Evaporation of the methylene chloride gave a residue which was crystallized from ethyl acetate to yield 1.3 g, mp 113°–116°.

TABLE I
PHYSICAL DATA

| R | X | Physical Constant |
|---|---|---|
| CH₃ | m-OH | b.p. 145°–155° (0.5 μ) |
| CH₃ | m-OCH₃ | b.p. 120° (0.3 μ) |
| CH₃ | p-F | b.p. 110° (0.15 nm) |
| —CH₂—CH=CH₂ | m-OH | b.p. 240° (0.2 μ) |
| —CH₂—CH=CH₂ | m-OCH₃ | b.p. 150° (0.05 nm) |
| —CH₂—CH=C(CH₃)₂ | m-OH | b.p. 240° (o.2 μ) |
| —C₅H₁₁ | m-OCCH₃ (O) | b.p. 100°–105° (1 μ) |
| —C₃H₁₁ | m-OCH₃ | b.p. 70° (1 μ) |
| —CH₂—◁ | m-OH | b.p. 160° (2 μ) |
| —CH₂—◁ | m-OCH₃ | b.p. 120°(1 μ) |
| —CH₂—◇ | m-OH | b.p. 180° (1 μ) m.p. 79°–81° |
| —CH₂—◇ | m-OCH₃ | b.p. 130°–135° (0.5 μ) |
| —CH₂CH₂—⌬ | m-OH | b.p. 200° (0.5 μ) m.p. 78°–80° |
| —CH₂CH₂—⌬ | m-OCH₃ | b.p. 140° (1 μ) |
| —CH₂CH₂—⌬—F | m-OCH₃ | b.p. 125° (0.3 μ) |
| —CH₂CH₂—⌬—F | m-OH | b.p. 170° (0.5 μ) |
| —CH₂CH₂—⌬—Cl | m-OH (HCl salt) | b.p. 200° (0.5 μ) |
| —CH₂CH₂—⌬—Cl | m-OCH₃ | b.p. 150°–156° (0.5 μ) |
| —CH₂CH₂—⌬—CH₃ | m-OH | b.p. 205°–210° (0.5 μ) |
| —CH₂CH₂—⌬—CH₃ | m-OCH₃ | b.p. 120°–130° (0.5 μ) |
| —CH₂CH₂—⌬—CH(CH₃)₂ | m-OH | b.p. 200°–210° (0.5 μ) |
| —CH₂CH₂—⌬—CH(CH₃)₂ | m-OCH₃ | b.p. 140°–145° (0.5 μ) |
| —CH₂CH₂—⌬—OCH₃ | m-OCH₃ | b.p. 165°–169° (0.4 μ) |
| —CH₂CH₂—⌬—N(CH₃)₂ | m-OCH₃ | b.p. 155°–160° (0.5 μ) |
| —CH₂CH₂—furyl(O) | m-OCH₃ | b.p. 140° (0.5 μ) |
| —CH₂CH₂—thienyl(S) | m-OH (HCl salt) | m.p. 100° (d) |
| —CH₂CH₂—thienyl(S) | m-OCH₃ | b.p. 150° (0.5 μ) |

TABLE I-continued
PHYSICAL DATA

[Structure: bicyclic compound with phenyl ring bearing X substituent, fused to cyclohexane with N—R group, H indicated]

| R | X | Physical Constant |
|---|---|---|
| —CH₂CH₂—[thiophene] | m-OCCH₃ (O=) | b.p. 150° (0.5 μ) |
| —CH₂CH₂CH₂CH₂—[phenyl] | m-OCH₃ | b.p. 150° (0.4 μ) |
| —CH₂CH₂—[phenyl-CH₃ with CH₃] | m-OH | b.p. 170°–180° (1μ) |

Dosage Forms and Use

The analgesic agents of this invention can be administered to alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 0.1 to 50, and preferably 1 to 25 milligrams per kilogram per day given in divided doses 2 to 4 times a day or in sustained release form is effective to obtain desired results.

Dosage forms (compositions) suitable for internal administration contain from about 25 milligrams to about 75 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a soluble oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

A standard procedure for detecting and comparing the analgesic activity of compounds in this series for which there is good correlation with human efficacy is the standard phenylquinone writhing test (PQW) modified from Siegmund, et al., *Proc. Soc. Exp. Biol. Med.* 95, 729 (1957). A test compound suspended in 1% methylcellulose was given orally to fasted (17–21 hours) female white mice, 5–20 animals per dose in a double blind test. Aqueous (0.01% phenyl-p-benzoquinone) phenylquinone was injected intraperitoneally at 23 or 30 minutes later using 0.20 ml per mouse. Commencing at 30 or 37 minutes, respectively, after the oral administration of the test compound, the mice were observed for 10 minutes for a characteristic stretching or writhing syndrome which is indicative of pain induced by phenylquinone. The effective analgesic dose for 50% of the mice (ED 50) was calculated by the moving average method of Weil, *Biometrics* 8, 249 (1952).

The following table shows the oral ED 50 dosages for analgesia (PQW test) of a number of compounds of the invention and several standard analgesics.

TABLE II
CIS-DECAHYDROISOQUINOLINE ANALGESICS

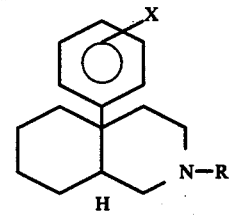

| R | X | PQW ED$_{50}$ (mg/kg) |
|---|---|---|
| —CH$_3$ | m-OH | 2.9 |
|  | m-OCH$_3$ | 14. |
| —CH$_2$—cyclopropyl | m-OH | 20. |
| —CH$_2$—cyclopropyl | m-OCH$_3$ | 18.5 |
| —CH$_2$—cyclobutyl | m-OH | 20. |
| —CH$_2$—cyclobutyl | m-OCH$_3$ | 14.5 |
| —CH$_2$CH$_2$—phenyl | m-OH | 21. |
| —CH$_2$CH$_2$—phenyl |  |  |
| —CH$_3$ | p-F | 26. |
| —CH$_2$—CH=CH$_2$ | m-OH | 43. |
| —CH$_2$—CH=C(CH$_3$)$_2$ | m-OH | 40. |
| —C$_5$H$_{11}$ | m-OCH$_3$ | 20. |
| —CH$_2$CH$_2$—C$_6$H$_4$—F | m-OCH$_3$ | 33. |
|  | m-OH | 28. |
| —CH$_2$CH$_2$—C$_6$H$_4$—Cl |  |  |
| —CH$_2$CH$_2$—C$_6$H$_4$—Cl | m-OCH$_3$ [HCl salt] | 16. |

TABLE II-continued
CIS-DECAHYDROISOQUINOLINE ANALGESICS

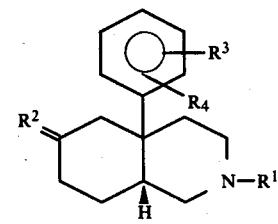

| R | X | PQW ED$_{50}$ (mg/kg) |
|---|---|---|
| —CH$_2$CH$_2$—C$_6$H$_4$—CH$_3$ | m-OH [HCl salt] | 9.7 |
| —CH$_2$CH$_2$—C$_6$H$_4$—CH$_3$ | m-OCH$_3$ | 11. |
| —CH$_2$CH$_2$—C$_6$H$_4$—N(CH$_3$)$_2$ | m-OCH$_3$ | 15.1 |
| —CH$_2$CH$_2$—furyl(O) | m-OCH$_3$ | 25. |
| —CH$_2$CH$_2$—thienyl(S) | m-OH [HCl salt] | 24. |
| —CH$_2$CH$_2$—thienyl(S) | m-OCH$_3$ | 27. |
| —CH$_2$CH$_2$—thienyl(S) | m—OCCH$_3$ (O) | 27. |

| STANDARD ANALGESICS | ED$_{50}$(mg/kg) |
|---|---|
| Morphine H$_2$SO$_4$ | 1.6 |
| Codeine H$_3$PO$_4$ | 8. |
| Nalbuphine HCl | 8.4 |
| Pentazocine HCl | 57. |
| Aspirin | 109. |

The following table gives data for additional compounds of the invention.

Table III

| Compound of Example | Mouse ED$_{50}$ mg/kg Analgesia (PQW)-Oral |
|---|---|
| 20-G | 28; 22 |
| 20-H | 6.7; 2.6 |
| 21 | 8.2; 3.4 |
| 22-C | 54 |
| 23 | 3.5 |
| 27-C | 10.8 |
| 28 | 61 |

I claim:

1. A compound having a cis configuration of the formula wherein $R^1 = (CH_2)_m$ 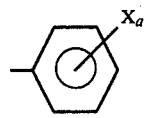

in which
m is 1 to 4,
X is Cl, Br, F, $CF_3$, $OCH_3$, $CH_3$, isopropyl, $-NH_2$ or $-N(CH_3)_2$ and
a = 0, 1 or 2;

$R^2 =$ 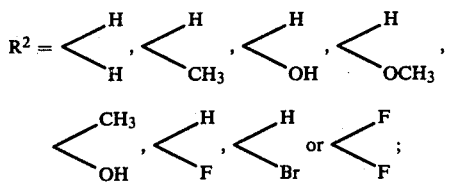

$R^3 = -OH, -OCH_3,$

or F; and
$R^4 = H, -OH, -OCH_3,$

with the proviso that when $R^3$ is $-F$, $R^4$ must be $-H$; or a pharmaceutically suitable salt thereof.

2. The compound of claim 1 where $R_2$ is

3. The compound of claim 1 where $R_2$ is

4. The compound of claim 1 where $R_3$ is m-$OCH_3$ and $R_4$ is H.

5. The compound of claim 1 where $R_1$ is

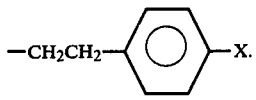

6. The compound of claim 1: N-phenethyl-4a-(m-methoxyphenyl)-cis-decahydroisoquinoline.

7. The compound of claim 1: N-phenethyl-4a-(m-hydroxyphenyl)-cis-decahydroisoquinoline.

8. The compound of claim 1: 6-methyl-N-(p-tolyl-β-ethyl)-4a-(m-hydroxyphenyl)-cis-decahydroisoquinoline.

9. The compound of claim 1: 6-methyl-N-(p-tolyl-β-ethyl)-4a-(m-methoxyphenyl)-cis-decahydroisoquinoline.

10. The compound of claim 1: N-(p-tolyl-β-ethyl)-4a-(m-hydroxyphenyl)-cis-decahydroisoquinoline hydrochloride salt.

11. The compound of claim 1: N-(p-tolyl-β-ethyl)-4a-(m-methoxyphenyl)-cis-decahydroisoquinoline.

12. A pharmaceutical analgesic composition comprising a suitable pharmaceutical carrier and a compound of claim 2.

13. A pharmaceutical analgesic composition comprising a suitable pharmaceutical carrier and a compound of claim 3.

14. A pharmaceutical analgesic composition comprising a suitable pharmaceutical carrier and a compound of claim 4.

15. A pharmaceutical analgesic composition comprising a suitable pharmaceutical carrier and a compound of claim 5.

16. A pharmaceutical analgesic composition comprising a suitable pharmaceutical carrier and a compound of claim 6.

17. A pharmaceutical analgesic composition comprising a suitable pharmaceutical carrier and a compound of claim 7.

18. A pharmaceutical analgesic composition comprising a suitable pharmaceutical carrier and a compound of claim 8.

19. A pharmaceutical analgesic composition comprising a suitable pharmaceutical carrier and a compound of claim 9.

20. A pharmaceutical analgesic composition comprising a suitable pharmaceutical carrier and a compound of claim 10.

21. A pharmaceutical analgesic composition comprising a suitable pharmaceutical carrier and a compound of claim 11.

22. A method of producing analgesia in a mammal which comprises internally administering to the mammal an effective analgesic amount of a compound of claim 2.

23. A method of producing analgesia in a mammal which comprises internally administering to the mammal an effective analgesic amount of a compound of claim 3.

24. A method of producing analgesia in a mammal which comprises internally administering to the mammal an effective analgesic amount of a compound of claim 4.

25. A method of producing analgesia in a mammal which comprises internally administering to the mammal an effective analgesic amount of a compound of claim 5.

26. A method of producing analgesia in a mammal which comprises internally administering to the mammal an effective analgesic amount of a compound of claim 6.

27. A method of producing analgesia in a mammal which comprises internally administering to the mammal an effective analgesic amount of a compound of claim 7.

28. A method of producing analgesia in a mammal which comprises internally administering to the mammal an effective analgesic amount of a compound of claim 8.

29. A method of producing analgesia in a mammal which comprises internally administering to the mammal an effective analgesic amount of a compound of claim 9.

30. A method of producing analgesia in a mammal which comprises internally administering to the mammal an effective analgesic amount of a compound of claim 10.

31. A method of producing analgesia in a mammal which comprises internally administering to the mammal an effective analgesic amount of a compound of claim 11.

* * * * *